United States Patent [19]

Manning et al.

[11] Patent Number: 4,772,586

[45] Date of Patent: * Sep. 20, 1988

[54] NOVEL DERIVATIVES OF ARGININE VASOPRESSIN ANTAGONISTS

[75] Inventors: Maurice Manning, Toledo, Ohio; Wilbur H. Sawyer, Scarsdale, N.Y.

[73] Assignees: Medical College of Ohio, Toledo, Ohio; Trustees of Columbia University, New York, N.Y.; a part interest

[*] Notice: The portion of the term of this patent subsequent to Mar. 12, 2004 has been disclaimed.

[21] Appl. No.: 947,725

[22] Filed: Dec. 30, 1986

Related U.S. Application Data

[63] Continuation-in-part of Ser. No. 693,870, Jan. 23, 1985, Pat. No. 4,649,130, which is a continuation-in-part of Ser. No. 574,257, Jan. 26, 1984, Pat. No. 4,714,696.

[51] Int. Cl.$^4$ .................. A61K 37/34; C07K 7/16
[52] U.S. Cl. ................... 514/11; 514/807; 530/315
[58] Field of Search ............ 530/315; 514/807, 11

[56] References Cited

U.S. PATENT DOCUMENTS

| | | |
|---|---|---|
| 4,285,858 | 8/1981 | Cort et al. .................. 530/315 |
| 4,543,349 | 9/1985 | Callahan et al. ........... 530/315 |
| 4,551,445 | 11/1985 | Manning et al. .......... 530/315 |
| 4,624,943 | 11/1986 | Callahan et al. ........... 530/315 |
| 4,649,130 | 3/1987 | Manning et al. .......... 530/315 |
| 4,656,248 | 4/1987 | Kalbag et al. .............. 530/315 |

OTHER PUBLICATIONS

Manning, M. et al., *Journal of Cardiovascular Pharmacology*, vol. 8, Suppl. 7 (1986).
Hruby, V. J. et al., *The Peptides*, vol. 8, pp. 77–207, Academic, Orlando, Fl. (1987).

*Primary Examiner*—Delbert R. Phillips
*Attorney, Agent, or Firm*—Emch, Schaffer, Schaub & Porcello Co.

[57] ABSTRACT

Compounds acting as antagonists of the antidiuretic-/and or vasopressor activity of arginine vasopressin are those of the formula

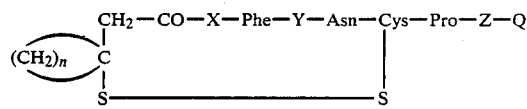

wherein n is 4 or 5; X is (D- or L-)Tyr(R), D-Phe, D-Val, D-Leu, D-Ile, D-Nva, D-Nle, D-Cha, D-Abu, D-Thr, D-Asn, D-Met or D-Gln; Y is Val, Ile, Thr, Ala, Lys, Cha, Nva, Met, Nle, Orn, Ser, Asn, Gln, Phe, Tyr, Gly, Abu or Leu; Z is (D- or L-) Arg, Orn or Lys; Q is Arg(NH$_2$), Ser(NH$_2$), (D- or L-)Ala(NH$_2$), Gly, OH or NH$_2$ and R is methyl, ethyl, propyl or butyl; provided that, when Y is Gln or Val, R may also be H. Further compounds are those wherein Q is NH(CH$_2$)$_{3-6}$NH$_2$, NH(CH$_2$)$_{2-6}$OH, NHalk or NHbzl, provided that when Y is Val, Q is other than NHalk or NHbzl. Other compounds are those wherein Q is M-P, wherein M is Gly, (D- or L-)beta-Ala, (D- or L-)Ala, Sar, Orn, Val, Phe, Ile, Thr, Pro, Tyr, Arg or Ser and P is NHalk, NHbzl, NH(CH$_2$)$_{2-6}$OH, NH(CH$_2$)$_{2-6}$NH$_2$ or OH, provided that when M is Gly, P is other than OH, and that when M is (D- or L-)beta-Ala, P is also NH$_2$. Further compounds include decapeptides wherein Q is M-A-P', wherein M and A are selected independently from Gly, (D- or L-)beta-Ala, (D- or L-)Ala, Sar, Orn, Val, Phe, Ile, Thr, Pro, Tyr, Arg or Ser and P' is OH, NH$_2$, NHalk, NH(CH$_2$)$_{2-6}$NH$_2$, NHbzl or NH(CH$_2$)$_{2-6}$OH. Additional compounds include those wherein X is D-Tyr.

69 Claims, No Drawings

NOVEL DERIVATIVES OF ARGININE VASOPRESSIN ANTAGONISTS

REFERENCE TO RELATED APPLICATION

This is a continuation-in-part of Manning et al., application Ser. No. 06/693,870, filed Jan. 23, 1985, now U.S. Pat. No. 4,649,130 which is a continuation-in-part of application Ser. No. 06/574,257, filed Jan. 26, 1984, now U.S. Pat. No. 4,714,696.

DESCRIPTION

The invention described herein was made in the course of work under a grant or award from the Department of Health and Human Services.

BACKGROUND OF THE INVENTION

This invention relates to novel peptides which antagonize the antidiuretic and/or vasopressor action of arginine vasopressin in vivo.

PRIOR ART STATEMENT

Attempts to develop clinically useful synthetic antagonists of in vivo antidiuretic and/or vasopressor responses to arginine vasopressin, the antidiuretic hormone (ADH), have led to the synthesis and pharmacological evaluation of hundreds of analogs of the neurohypophysial peptides, oxytocin and vasopressin.

Analogs of vasopressin or oxytocin which antagonize antidiuretic responses to ADH have been reported by Chan et al., *Science*, vol. 161 (1968) at 280 and *J. Pharmacol. Exp. Ther.*, vol. 174 (1974) at 541 and vol. 196 (1976) at 746; Dousa et al., *Science*, vol. 167 (1970) at 1134; Nestor et al., *J. Med. Chem.*, vol. 18 (1975) at 1022 and Larsson et al., *J. Med. Chem.*, vol. 21 (1978) at 352, herein incorporated by reference. None of the compounds reported has been pharmacologically or clinically useful as an antidiuretic antagonist.

The synthesis and evaluation of vasopressin analogs, incorporating etherified tyrosine at the 2-position, valine at the 4-position and D- or L-arginine at the 8-position, which antagonize the antidiuretic action of ADH in vivo, have been reported by Sawyer et al., *Science*, vol. 212 (1981) at 49; Manning et al., *J. Med. Chem.*, vol. 24 (1981) at 701; and Manning et al., U.S. Pat. Nos. 4,367,225 and 4,399,125, herein incorporated by reference.

The synthesis of arginine vasopressin derivatives, containing unetherified tyrosine at the 2-position, has been described by Manning et al., "Studies Leading to Orally Active Antagonists of the Antidiuretic (V$_2$) and Vasopressor (V$_1$) Responses to Arginine Vasopressin," *Proc. 9th Amer. Pep. Symp.*, Hruby et al., eds., Pierce Chemical Co., Rockford, Ill. (1985) at 599–602.

The effect of variation in the amino acid at the 4-position of arginine vasopressin has been investigated by Manning et al., *J. Med. Chem.*, vol. 26 (1983) at 1607 and in U.S. Pat. No. 4,551,445.

Design of tissue-specific agonists and antagonists in the field of neurohypophysial peptides has been considered by Sawyer et al., *Molecular and Cellular Endocrinology*, vol. 22 (1981), 117–134; Manning et al., "The Pituitary," Beardwell et al., eds., Butterworths, Kent, England (1981), 265–296; Manning et al., "Peptides, Synthesis, Structure, Function," Rich et al., eds., Pierce Chemical Co., (1981) at 257–260 and Manning et al., *J. Med. Chem.*, vol. 25 (1982) at 45 and 414.

Modification of oxytocin, containing a D-amino acid at the 2-position has been disclosed by Lebl et al., *Peptides*, Walter de Gruyter & Co., Berlin (1983), at 457. Other modifications, having a penicillamine unit at the 1- and 6-positions of vasopressin, have been disclosed by Simek et al., ibid, at 461. Modification of vasopressin analogs at the 9-position, for example, 1-deamino[9-D-alananimide]AVP, has been investigated by Gazis et al., ibid., at 465. In the latter article, retention of significant antidiuretic activity of vasopressins, having 9-(D- or L-) alaninamide groups is recited, but the compounds have markedly decreased pressor activity. See also Buku et al., *Int. J. Peptide Res.*, vol. 23 (1984), at 551.

Brtnik et al., *Coll. Czech. Chem. Comm.*, vol. 48 (1983) at 2862 disclose modification of vasopressin by removal of glycine at the 9-position and replacement of D-Arg at the 8-position by basic non-coded amino acids. These compounds have almost no uterotonic, pressor or antidiuretic activity. Toth et al., *Acta Physcia et Chimica*, vol. 29 (1983) at 187, report the synthesis of three analogues of deamino-vasopressin, lacking the C-terminal glycinamide group. Cort et al. have proposed, in U.S. Pat. No. 4,285,858, that vasopressin analogs having a configuration of L-Arg-D-AlaNH$_2$ or D-Arg-L-AlaNH$_2$ at the 8- or 9-positions have very weak antidiuretic or pressor activity.

Huffman et al. (U.S. Pat. No. 4,469,679) recite the preparation of octapeptide vasopressin antagonists.

However, Manning et al., *Nature*, vol. 308 (1984) at 652, have found that the carboxy terminus of vasopressin is required for agonist activity, but not for binding.

It is therefore apparent that the correlation between structure of neurohypophysial peptides and action in vivo is not well understood and there is a continuing need for the development of pharmacologically and clinically effective antagonists of the antidiuretic action of arginine vasopressin.

OBJECT OF THE INVENTION

It is the object of the invention to provide novel antagonists of the antidiuretic and/or vasopressor action of ADH, which are effective in vivo.

SUMMARY OF THE INVENTION

This invention relates to novel antagonists of the antidiuretic and/or vasopressor action of ADH, which are compounds of the General Formula:

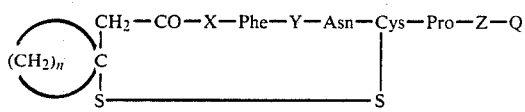

wherein n is 4 or 5; X is (D- or L-)Tyr(R), D-Phe, D-Val, D-Ile, D-Nva, D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Cln, Phe, Tyr, Gly, Abu, or Leu; Z is (D- or L-)Arg, Orn or Lys; Q is Arg(NH$_2$), Ser(NH$_2$), (D- or L-)Ala(NH$_2$), Gly, OH or NH$_2$ and R is methyl, ethyl, propyl or butyl; provided that when Y is Gln or Val, R may also be H.

Other compounds of this invention are those wherein Q is NH(CH$_2$)$_{3-6}$NH$_2$ or NH(CH$_2$)$_{2-6}$OH, NHalk or NHbzl, provided that when Y is Val, Q is other than NHalk or NHbzl.

Additional compounds of this invention are nonapeptides, in which Q is M-P and the terminal sequence is Pro-Z-M-P. In these compounds, M is Gly, (D- or L-) beta-Ala, (D- or L-)Ala, Sar, Orn, Val, Phe, Ile, Thr, Pro, Tyr, Arg or Ser, and P is $NH(CH_2)_{2-6}NH_2$, $NH(CH_2)_{2-6}OH$, NHalk, NHbzl or OH, provided that when P is OH, M is other than Gly.

Further compounds of this invention are decapeptides in which Q is M-A-P'. The terminal sequence of amino acids is Pro-Z-M-A-P'. M and and A are selected independently from Gly, Orn, Val, Phe, Ile, Arg, Ser, Thr, Pro, (D- or L-)Ala, (D- or L-)beta-Ala, Sar or Tyr and P' is $NH_2$, OH, NHalk, NHbzl, $NH(CH_2)_{2-6}NH_2$ or $NH(CH_2)_{2-6}OH$.

The compounds of this invention further comprise some compounds in which X is D-Tyr.

This invention further relates to a method for antagonizing the in vivo antidiuretic and/or vasopressor response to ADH, comprising administering to an animal being treated an amount of a compound of the General Formula, in admixture with a physiologically and pharmaceutically accepable carrier, effective to antagonize the antidiuretic and/or vasopressor response to ADH.

DETAILED DESCRIPTION

Compounds of the invention, or comparison compounds of the prior art, are derivatives of arginine vasopressin. Amino acids are in the L-form, unless otherwise indicated. Each symbol, except for that of the 9-terminal substituent, is for the acyl (—C=O—) residue of the designated amino acid. For example, 9-OH represents a compound with a completed —COOH group of the amino acid residue at the 8-position and is, therefore, a desglycinamide compound. The correlation between full names and abbreviations is:

AVP, arginine vasopressin;
AVP-acid, deamido-arginine vasopressin, alternatively, vasopressinoic acid;
desGly$^9$-AVP, 9-desglycine-argoinine vasopressin;
desGly(NH$_2$)$^9$AVP, 9-desglycinamide-arginine vasopressin;
d(CH$_2$)$_5$AVP, [1-(beta-mercapto-beta,beta-cyclopentamethylenepropionic acid)]-arginine vasopressin;
d(CH$_2$)$_5$VDAVP, [1-(beta-mercapto-beta,beta-cyclopentamethylenepropionic acid), 4-valine, 8-D-arginine]vasopressin;
d(CH$_2$)$_5$Tyr(Me)VDAVP, [1-(beta-mercapto-beta,beta-cyclopentamethylenepropionic acid), 2-O-methyltyrosine, 4-valine, 8-D-arginine]vasopressin;
d(CH$_2$)$_5$-D-TyrVDAVP, [1-(beta-mercapto-beta,beta-cyclopentamethylenepropionic acid), 2-D-tyrosine, 4-valine, 8-D-arginine]vasopressin;
d(CH$_2$)$_5$-D-TyrVAVP, [1-(beta-mercapto-beta,beta-cyclopentamethylenepropionic acid), 2-D-tyrosine, 4-valine]-arginine vasopressin;
d(CH$_2$)$_5$Tyr(Me)AVP, [1-(beta-mercapto-beta,beta-cyclopentamethylenepropionic acid), 2-O-methyltyrosine]-arginine vasopressin;
desGly$^9$d(CH$_2$)$_5$AVP, [1-(beta-mercapto-beta,beta-cyclopentamethylenepropionic acid), 9-desglycine]-arginine vasopressin;
desGly(NH$_2$)$^9$d(CH$_2$)$_5$AVP, [1-(beta-mercapto-beta,beta-cyclopentamethylenepropionic acid), 9-desglycinamide]-arginine vasopressin;
d(CH$_2$)$_5$[D-Phe$^2$]VAVP, [1-(beta-mercapto-beta,beta-cyclopentamethylenepropionic acid), 2-D-phenylalanine, 4-valine]-arginine vasopressin;
desGly$^9$d(CH$_2$)$_5$[D-Phe$^2$]VAVP, [1-(beta-mercapto-beta,beta-cyclopentamethylenepropionic acid), 2-D-phenylalanine, 4-valine, 9-desglycine]-arginine vasopressin;
desGly(NH$_2$)$^9$d(CH$_2$)$_5$[D-Phe$^2$]VAVP, [1-(beta-mercapto-beta,beta-cyclopentamethylenepropionic acid), 2-D-phenylalanine, 4-valine, 9-desglycinamide]-arginine vasopressin;
d(CH$_2$)$_5$[D-Phe$^2$, Ile$^4$]AVP, [1-(beta-mercapto-beta,beta-cyclopentamethylenepropionic acid), 2-D-phenylalanine, 4-isoleucine]-arginine vasopressin;
desGly$^9$d(CH$_2$)$_5$[D-Phe$^2$, Ile$^4$]AVP, [1-(beta-mercapto-beta,beta-cyclopentamethylenepropionic acid), 2-D-phenylalanine, 4-isoleucine, 9-desglycine]-arginine vasopressin;
d(CH$_2$)$_5$[D-Tyr(Et)$^2$]VAVP, [1-(beta-mercapto-beta,beta-cyclopentamethylenepropionic acid), 2-D-(O-ethyl)tyrosine, 4-valine]-arginine vasopressin;
desGly$^9$d(CH$_2$)$_5$[D-Tyr(Et)$^2$]VAVP, [1-(beta-mercapto-beta,beta-cyclopentamethylenepropionic acid), 2-D-(O-ethyl)tyrosine, 4-valine, 9-desglycine]-arginine vasopressin;
d(CH$_2$)$_5$[D-Phe$^2$, Ile$^4$, Arg-NH$_2^9$]AVP, [1-(beta-mercapto-beta,beta-cyclopentamethylenepropionic acid), 2-D-phenylalanine, 4-isoleucine, 9-argininamide]-arginine vasopressin;
d(CH$_2$)$_5$[D-Phe$^2$, Ile$^4$, Ser-NH$_2^9$]AVP, [1-(beta-mercapto-beta,beta-cyclopentamethylenepropionic acid), 2-D-phenylalanine, 4-isoleucine, 9-serinamide]-arginine vasopressin;
d(CH$_2$)$_5$[D-Phe$^2$, Ile$^4$, Ala-NH$_2^9$]AVP, [1-(beta-mercapto-beta,beta-cyclopentamethylenepropionic acid), 2-D-phenylalanine, 4-isoleucine, 9-alaninamide]-arginine vasopressin;
d(CH$_2$)$_5$[D-Phe$^2$, Ile$^4$, D-Ala-NH$_2^9$]AVP, [1-(beta-mercapto-beta,beta-cyclopentamethylenepropionic acid), 2-D-phenylalanine, 4-isoleucine, 9-D-alaninamide]-arginine vasopressin;
d(CH$_2$)$_5$[D-Phe$^2$, Ile$^4$, Orn-NH$_2^9$]AVP, [1-(beta-mercapto-beta,beta-cyclopentamethylenepropionic acid), 2-D-phenylalanine, 4-isoleucine, 9-ornithinamide]-arginine vasopressin;
desGly(NH$_2$)$^9$d(CH$_2$)$_5$[D-Phe$^2$, Ile$^4$, Arg(NHCH$_2$CH$_2$NH$_2$)$^8$]AVP, [1-(beta-mercapto-beta,beta-cyclopentamethylenepropionic acid), 2-D-phenylalanine, 4-isoleucine, 8-arginine-N-beta-aminoethylamide, 9-desglycinamide]-arginine vasopressin;
d(CH$_2$)$_5$[D-Phe$^2$, Ile$^4$, Val-NH$_2^9$]AVP, [1-(beta-mercapto-beta,beta-cyclopentamethylenepropionic acid), 2-D-phenylalanine, 4-isoleucine, 9-valinamide]-arginine vasopressin;
d(CH$_2$)$_5$[D-Phe$^2$, Ile$^4$, Phe-NH$_2^9$]AVP, [1-(beta-mercapto-beta,beta-cyclopentamethylenepropionic acid), 2-D-phenylalanine, 4-isoleucine, 9-phenylalaninamide]-arginine vasopressin;
d(CH$_2$)$_5$[D-Phe$^2$, Ile$^4$, Ile-NH$_2^9$]AVP, [1-(beta-mercapto-beta,beta-cyclopentamethylenepropionic acid), 2-D-phenylalanine, 4-isoleucine, 9-isoleucinamide]-arginine vasopressin;
d(CH$_2$)$_5$[D-Phe$^2$, Ile$^4$, Thr-NH$_2^9$]AVP, [1-(beta-mercapto-beta,beta-cyclopentamethylenepropionic acid), 2-D-phenylalanine, 4-isoleucine, 9-threoinamide]-arginine vasopressin;
d(CH$_2$)$_5$[D-Phe$^2$, Ile$^4$, Pro-NH$_2^9$]AVP, [1-(beta-mercapto-beta,beta-cyclopentamethylenepropionic acid), 2-D-phenylalanine, 4-isoleucine, 9-prolinamide]-arginine vasopressin;

d(CH$_2$)$_5$[D-Phe$^2$, Ile$^4$, Tyr-NH$_2$$^9$]AVP, [1-(beta-mercapto-beta,beta-cyclopentamethylenepropionic acid), 2-D-phenylalanine, 4-isoleucine, 9-tyrosinamide]-arginine vasopressin;

desGly(NH$_2$)$^9$d(CH$_2$)$_5$[D-Tyr(Et)$^2$]VAVP, [1-(beta-mercapto-beta,beta-cyclopentamethylenepropionic acid), 2-D-(O-ethyl)tyrosine, 4-valine, 9-desglycinamide]-arginine vasopressin;

desGly(NH$_2$)$^9$d(CH$_2$)$_5$[D-Phe$^2$, Ile$^4$]AVP, [1-(beta-mercapto-beta,beta-cyclopentamethylenepropionic acid), 2-D-phenylalanine, 4-isoleucine, 9-desglycinamide]-arginine vasopressin;

d(CH$_2$)$_5$[Tyr(Et)$^2$]VAVP, [1-(beta-mercapto-beta,beta-cyclopentamethylenepropionic acid), 2-(O-ethyl)tyrosine, 4-valine]-arginine vasopressin;

desGly$^9$d(CH$_2$)$_5$[Tyr(Et)$^2$]VAVP, [1-(beta-mercapto-beta,beta-cyclopentamethylenepropionic acid), 2-(O-ethyl)tyrosine, 4-valine, 9-desglycine]-arginine vasopressin;

d(CH$_2$)$_5$[D-Phe$^2$, Ile$^4$]AVP acid, [1-(beta-mercapto-beta,beta-cyclopentamethylenepropionic acid), 2-D-phenylalanine, 4-isoleucine, 9-glycine]-arginine vasopressin, alternatively, [1-(beta-mercapto-beta,beta-cyclopentamethylenepropionic acid), 2-D-phenylalanine, 4-isoleucine]arginine vasopressinoic acid;

desGly$^9$d(CH$_2$)$_5$[Tyr(Me)$^2$]AVP, [1-(beta-mercapto-beta,beta-cyclopentamethylenepropionic acid), 2-(O-methyl)tyrosine, 9-desglycine]-arginine vasopressin;

desGly(NH$_2$)$^9$d(CH$_2$)$_5$[Tyr(Me)$^2$]AVP, [1-(beta-mercapto-beta,beta-cyclopentamethylenepropionic acid, 2-(O-methyl)tyrosine, 9-desglycinamide]-arginine vasopressin;

d(CH$_2$)$_5$[Tyr(Me)$^2$, Ala(NH$_2$)$^9$]AVP, [1-(beta-mercapto-beta,beta-cyclopentamethylenepropionic acid), 2-(O-methyl)tyrosine, 9-alaninamide]-argine vasopressin;

desGly(NH$_2$)$^9$d(CH$_2$)$_5$[D-Phe$^2$, Ile$^4$, Arg(NHCH$_2$CH$_2$OH)$^8$]VP, [1-(beta-mercapto-beta,beta-cyclopentamethylenepropionic acid), 2-D-phenylalanine, 4-isoleucine, 8-arginine-N-(beta-hydroxy)ethylamide, 9-desglycinamide] vasopressin;

desGly(NH$_2$)$^9$d(CH$_2$)$_5$[D-Tyr(Et)$^2$, Ile$^4$, Arg)(NHCH$_2$CH$_2$OH)$^8$]VP, [1-(beta-mercapto-beta,beta-cyclopentamethylenepropionic acid), 2-D-(O-ethyl)tyrosine, 4-isoleucine, 8-arginine-N-(beta-hydroxy)ethylamide, 9-desglycinamide] vasopressin;

desGly(NH$_2$)$^9$d(CH$_2$)$_5$[D-Phe$^2$, Ile$^4$, Arg(NH(CH$_2$)$_4$NH$_2$)$^8$]VP, [1-(beta-mercapto-beta,beta-cyclopentamethylenepropionic acid), 2-D-phenylalanine, 4-isoleucine, 8-arginine-N-(delta-amino)butylamide, 9-desglycinamide] vasopressin;

desGly(NH$_2$)$^9$d(CH$_2$)$_5$[D-Tyr(Et)$^2$, Ile$^4$, Arg(NH(CH$_2$)$_4$NH$_2$)$^8$]VP, [1-(beta-mercapto-beta,beta-cyclopentamethylenepropionic acid), 2-D-(O-ethyl)tyrosine, 4-isoleucine, 8-arginine-N-(delta-amino)butylamide, 9-desglycinamide] vasopressin;

desGly(NH$_2$)$^9$d(CH$_2$)$_5$[D-Phe$^2$, Ile$^4$, Arg(NHC$_4$H$_9$-n)$^8$]VP, [1-(beta-mercapto-beta,beta-cyclopentamethylenepropionic acid), 2-D-phenylalanine, 4-isoleucine, 8-arginine-N-(n-butyl)amide, 9-desglycinamide)] vasopressin;

desGly(NH$_2$)$^9$d(CH$_2$)$_5$[D-Tyr(Et)$^2$, Ile$^4$, Arg(NHC$_4$H$_9$-n)$^8$]VP, [1-beta-mercapto-beta,beta-cyclopentamethylenepropionic acid), 2-(D-O-ethyl)tyrosine, 4-isoleucine, 8-arginine-N-(n-butyl)amide, 9-desglycinamide] vasopressin;

desGly(NH$_2$)$^9$d(CH$_2$)$_5$[D-Tyr$^2$, Ile$^4$, Arg(NHCH$_2$CH$_2$NH$_2$)$^8$]VP, [1-beta-mercapto-beta,beta-cyclopentamethylenepropionic acid, 2-D-tyrosine, 4-isoleucine, 8-arginine-N-(beta-amino)ethylamide, 9-desglycinamide] vasopressin;

desGly(NH$_2$)$^9$d(CH$_2$)$_5$[D-Tyr$^2$, Ile$^4$, Arg(NHCH$_2$CH$_2$NH$_2$)$^8$]VP, [1-(beta-mercapto-beta,beta-cyclopentamethylenepropionic acid), 2-D-tyrosine, 4-isoleucine, 9-arginine-N-(beta-amino)ethylamide, 9-desglycinamide] vasopressin;

desGly(NH$_2$)$^9$d(CH$_2$)$_5$[D-Tyr(Et)$^2$, Ile$^4$, Arg(NHCH$_2$CH$_2$NH$_2$)$^8$]VP, [1-(beta-mercapto-beta,beta-cyclopentamethylenepropionic acid), 2-D-(O-ethyl)tyrosine, 4-isoleucine, 8-arginine-N-(beta-amino)ethylamide, 9-desglycinamide] vasopressin;

desGly(NH$_2$)$^9$d(CH$_2$)$_5$[D-Phe$^2$, Ile$^4$]AVP, [1-(beta-mercapto-beta,beta-cyclopentamethylenepropionic acid), 2-D-phenylalanine, 4-isoleucine, 9-desglycinamide]-arginine vasopressin;

desGly(NH$_2$)$^9$d(CH$_2$)$_5$[D-Phe$^2$, Ile$^4$, Arg(NHCH$_2$CH$_2$NH$_2$)$^8$]VP, [1-(beta-mercapto-beta,beta-cyclopentamethylenepropionic acid), 2-D-phenylalanine, 4-isoleucine, 8-arginine-N-(beta-amino)ethylamide, 9-desglycinamide] vasopressin;

desGly(NH$_2$)$^9$d(CH$_2$)$_5$[Tyr(Me)$^2$, Arg(NHCH$_2$CH$_2$NH$_2$)$^8$]VP, [1(beta-mercapto-beta,beta-cyclopentamethylenepropionic acid), 2-(O-methyl)tyrosine, 8-arginine-N-(beta-amino)ethylamide, 9-desglycinamide] vasopressin;

desGly(NH$_2$)$^9$d(CH$_2$)$_5$[Tyr(Me)$^2$, Arg(NHMe)$^8$]VP, [1-(beta-mercapto-beta,beta-cyclopentamethylenepropionic acid), 2-(O-methyl)tyrosine, 8-arginine-N-methylamide, 9-desglycinamide] vasopressin;

d(CH$_2$)$_5$[D-Tyr(Et)$^2$, Val$^4$, Gly(NHCH$_2$CH$_2$NH$_2$)$^9$]AVP, [1-(beta-mercapto-beta,beta-cyclopentamethylenepropionic acid), 2-D-(O-ethyl)tyrosine, 4-valine, 9-glycine-N-(beta-amino)ethylamide]-arginine vasopressin;

d(CH$_2$)$_5$[D-Phe$^2$, Ile$^4$, Gly(NHCH$_2$CH$_2$NH$_2$)$^9$]AVP, [1-(beta-mercapto-beta,beta-cyclopentamethylenepropionic acid), 2-D-phenylalanine, 4-isoleucine, 9-glycine-N-(beta-amino)ethylamide]-arginine vasopressin;

d(CH$_2$)$_5$[Tyr(Me)$^2$, Gly(NHCH$_2$CH$_2$NH$_2$)$^9$]AVP, [1-(beta-mercapto-beta,beta-cyclopentamethylenepropionic acid), 2-(O-methyl)tyrosine, 9-glycine-N-(beta-amino)ethylamide]-arginine vasopressin;

d(CH$_2$)$_5$[D-Phe$^2$, Ile$^4$, Gly(NHMe)$^9$]AVP, [1-(beta-mercapto-beta,beta-cyclopentamethylenepropionic acid), 2-D-phenylalanine, 4-isoleucine, 9-glycine-N-methylamide]-arginine vasopressin;

d(CH$_2$)$_5$[D-Tyr(Et)$^2$, Val$^4$, Gly(NHMe)$^9$]AVP, [1-(beta-mercapto-beta,beta-cyclopentamethylenepropionic acid), 2-D-(O-ethyl)tyrosine, 4-valine, 9-glycine-N-methylamide]-arginine vasopressin;

d(CH$_2$)$_5$[D-Tyr(Et)$^2$, Val$^4$, beta-Ala(NHMe)$^9$]AVP, 1-(beta-mercapto-beta,beta-cyclopentamethylene-proprionic acid), 2-D-(O-ethyl)tyrosine, 4-valine, 9-beta-alanine-N-methylamide]-arginine vasopressin;

d(CH$_2$)$_5$[D-Tyr(Et)$^2$, Val$^4$, Ala(NH$_{Me}$)$^9$]AVP, [1-(beta-mercapto-beta,beta-cyclopentamethylene-propionic acid), 2-D-(O-ethyl)tyrosine, 4-valine, 9-alanine-N-methylamide]-arginine vasopressin;

d(CH$_2$)$_5$[D-Ile$^2$, Ile$^4$, Gly(NHEt)$^9$]AVP, [1-(beta-mercapto-beta,beta-cyclopentamethylenepropionic acid), 2-D-isoleucine, 4-isoleucine, 9-glycine-N-ethylamide]-arginine vasopressin;

d(CH$_2$)$_5$[D-Phe$^2$, Ile$^4$, Gly(NHCH$_2$CH$_2$OH)$^9$]AVP, [1-(beta-mercapto-beta,beta-cyclopentamethylene-propionic acid), 2-D-phenylalanine, 4-isoleucine, 9-glycine-N-(beta-hydroxy)ethylamide]-arginine vasopressin;

d(CH$_2$)$_5$[D-Phe$^2$, Ile$^4$, Gly(NHCH$_2$CH$_2$NH$_2$)$^9$]AVP, [1-beta-mercapto-beta,beta-cyclopentamethylene-propionic acid), 2-D-phenylalanine, 4-isoleucine, 9-glycine-N-(beta-amino)ethylamide]-arginine vasopressin;

d(CH$_2$)$_5$[D-Tyr(Et)$^2$, Ile$^4$, Gly(NHCH$_2$CH$_2$NH$_2$)-$^9$]AVP, [1-(beta-mercapto-beta,beta-cyclopentamethylenepropionic acid), 2-D-(O-ethyl)tyrosine, 4-isoleucine, 9-glycine-N-(beta-amino)ethylamide]-arginine vasopressin;

d(CH$_2$)$_5$[D-Phe$^2$, Ile$^4$, Gly(NHBu-n)$^9$]AVP, [1-(beta-mercapto-beta,beta-cyclopentamethylenepropionic acid), 2-D-phenylalanine, 4-isoleucine, 9-glycine-N-(n-butyl)amide]-arginine vasopressin;

d(CH$_2$)$_5$[Tyr(Me)$^2$, Gly(NHBu-n)$^9$]AVP, [1-(beta-mercapto-beta,beta-cyclopentamethylenepropionic acid), 2-(O-methyl)tyrosine, 9-glycine-N-(n-butyl)amide]-arginine vasopressin;

d(CH$_2$)$_5$[Tyr(Me)$^2$, Gly(NHCH$_2$CH$_2$NH$_2$)$^9$]AVP, [1-(beta-mercapto-beta,beta-cyclopentamethylene-propionic acid), 2-(O-methyl)tyrosine, 9-glycine-N-(beta-amino)ethylamide]-arginine vasopressin;

d(CH$_2$)$_5$-[Tyr(Me)$^2$, Sar(NHMe)$^9$]VP, [1-(beta-mercapto-beta,beta-cyclopentamethylenepropionic acid), 2-O-methyltyrosine, 9-sarcosine-N-methylamide]-arginine vasopressin and d(CH$_2$)$_5$[D-Phe$^2$, Ile$^4$, Gly$^9$]AVP-Gly(NH$_2$), [1-(beta-mercapto-beta,beta-cyclopentamethylene-propionic acid), 2-D-phenylalanine, 4-isoleucine, 9-glycine]-arginine vasopressinyl glycinamide.

Alternative nomenclature for a representative compound, desGly$^9$d(CH$_2$)$_5$-AVP, is 9-desglycine-[1-beta-mercapto-beta,beta-cyclopentamethylenepropionic acid)]-arginine vasopressin.

Compounds of this invention, corresponding to Group A, include those of the General Formula wherein n is 4 or 5; X is (D- or L-)Tyr(R), D-Phe, D-Val, D-Leu, D-Ile, D-Nva, D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Gln, Phe, Tyr, Gly, Abu or Leu; Z is (D- or L)Arg, Orn or Lys; Q is NH(CH$_2$)$_p$NH$_2$, NH(CH$_2$)$_q$OH, NHalk or NHBzl; R is methyl, ethyl, propyl or butyl; p is an integer from 3 to 6; q is an integer from 2 to 6; and alk is methyl, ethyl, propyl or butyl, provided that when Y is Val, Q is other than NH alk or NHbzl.

Compounds of Group B of this invention are those of the General Formula wherein n is 4 or 5; X is (D- or L-)TYr(R), D-Phe, D-Val, D-Leu, D-Ile, D-Nva, D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Gln, Phe, Try, Gly, Abu or Leu; Z is (D- or L-)Arg, Orn or Lys; Q is M-P; M is Gly, (D- or L-)beta-Ala, (D- or L-)Ala, Sar, Orn, Val, Phe, Ile, Thr, Pro, Tyr, Arg or Ser; P is NHalk, NHbzl, NH(CH$_2$)$_{2-6}$NH$_2$, NH(CH$_2$)$_{2-6}$OH, or OH; R is H, methyl, ethyl, propyl or butyl; and alk is methyl, ethyl, propyl or butyl, provided that when M is Gly, P is other than OH and that when M is (D- or L-)-beta-Ala or Sar, P is also NH$_2$.

Compounds of Group C of the General Formula are those wherein the terminal sequence of amino acids is Pro-Z-M-A-P'(Q is M-A-P') and wherein n is 4 or 5; X is (D- or L-)Tyr(R), D-Phe, D-Val, D-Leu, D-Ile, D-Nva, D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Gln, Phe, Tyr, Gly, Abu or Leu, Z is (D- or L-)Arg, Orn or Lys; M and A are selected independently from Gly, Orn, Val, Phe, Ile, Arg, Ser, Thr, Pro, (D- or L-)Ala, (D- or L-)beta-Ala, Sar or Tyr; R is H, methyl, ethyl, propyl or butyl; and P' is OH, NH$_2$, NH$_2$, NHalk, NHbzl, NH(CH$_2$)$_{2-6}$NH$_2$ or NH(CH$_2$)$_{2-6}$OH.

Compounds of Group D of the General Formula are those wherein X is D-Tyr; n is 4 or 5; Y is Ile, Thr, Ala, Lys, Cha, Nva, Met, Nle, Orn, Ser, Asn, Phe, Tyr, Gly, Abu or Leu; Z is (D- or L-)Arg, Orn or Lys; and Q is NH(CH$_2$)$_{2-6}$NH$_2$ or NH-(CH$_2$)$_{2-6}$OH.

The active peptides were synthesized by solid phase synthesis, as described by Bankowski et al. (1978), infra; Merrifield, *J. Am. Chem. Soc.*, vol. 85 (1963) at 2149 and *Biochemistry*, vol. 3 (1964) at 1385; Manning, *J. Am. Chem. Soc.*, vol. 90 (1968) at 1348; Manning et al., *J. Med. Chem.*, vol. 19 (1976) at 376; Lowbridge et al., *J. Med. Chem.*, vol. 20 (1977) at 1173; Manning et al., *J. Med. Chem.*, vol. 16 (1973) at 975; Kruszynski et al. (1980), infra; Sawyer et al., (1981), supra or Manning et al. (1981), supra.

Compounds of the 9-desglycinamide group (Group A), that is, Q is NH$_2$, NH(CH$_2$)$_p$NH$_2$, NH(CH$_2$)$_q$OH or the the like, are prepared as for other arginine vasopressin derivatives, except that one less cycle of deprotection, neutralization and coupling is employed. That is, the first amino acid residue, attached to resin, will be (D- or L-) Arg, for example, rather than Gly, as would be the case for compounds in which Q is to be GlyNH$_2$. Cleavage is carried out by methods in the literature, using the appropriate amine or diamine. See Manning, supra, or Glass et al., *J. Med. Chem., vol.* 16 (1973), page 160, for example.

Compounds in which the amino acid at the 9-position is other than Gly(NH$_2$) are prepared in a similar fashion, but by attaching an amino acid other than glycine to the resin at the start of the synthesis. An alternative approach to these compounds was by cleavage of a protected octapeptide resin with HBr/TFA as described by Walter et al., *J. Med. Chem.,* vol 19 (1976) at 376. After purification of the resulting intermediate, the desired protected nonapeptide was obtained by an 8+1 coupling in solution.

Desglycinamide compounds, that is Q is OH, in accordance with this invention are prepared as described in the examples.

Decapeptides terminated by GlyNH$_2$ or alkylated glycinamide functions are prepared as above, starting, for example, from Gly-Gly-resin.

The discovery of the antidiuretic antagonists d(CH$_2$)$_5$Tyr(alk)VAVP, Sawyer et al. (1981), supra, and Manning et al. (1981), supra, led to the synthesis of various analogs having a cyclopentamethylene ring structure and various substituents at the 2-position. Other modifications at the 4-, 6-, 7- and 8-positions, have been proposed.

It will also be understood that alk and alkyl substituents (R) can be linear or branched and contemplated equivalents include all possible isomers. In the specification and claims, "bzl" means benzyl.

Compounds of this invention, having an action antagonistic toward the antidiuretic action of arginine vasopressin, are generally those wherein the 2-substituent is an amino acid of the D-series and the 4-substituent is an aliphatic amino acid.

Most of compounds of the General Formula are accordingly very effective antagonists of the antidiuretic response to ADH. They can therefore be used in pharmacological studies on the contribution of ADH to a variety of pathological states involving water retention. It is further contemplated that they could be effective and specific agents for treating the syndrome of inappropriate secretion of ADH, that is, the Schwartz-Bartter syndrome or SIADH. This syndrome can complicate a number of disorders, including carcinomas, pulmonary diseases, intracranial diseases and head injuries, Bartter et. al., *Am. J. Med.*, vol. 42 (1976) at 790. In addition, compounds of the General Formula are effective as antagonists of the vasopressor response to ADH.

Surprisingly, activity of the compounds of the invention as antagonists of ADH or vasopressin is not lost by removal or modification of the 9-substituent or by extension of the peptide chain to a decapeptide in which the terminal substituted is Gly or an amide thereof. It is known that the chemical bond between the 8- and 9-positions is at least one point at which digestive enzymes, such as trypsin, attack vasopressin-type hormones. Therefore, compounds of this invention, if not themselves entirely stable toward digestive enzymes, will be useful in suggesting routes to peptide derivatives which will retain their activity when administered orally. A representative compound, wherein n is 5, X is D-Phe, Y is Ile, Z is Arg and Q is $NHCH_2CH_2NH_2$, has been found orally active when administered to rats.

Retention of antagonist activity following hydrolysis of the C-terminal glycinamide of arginine vasopressin compounds, in accordance with this invention, is highly unexpected, in view of tryptic digestion of AVP to give 9-desglycinamide-AVP, which had neither the antidiuretic nor the vasopressor activity, characteristic of AVP. See, du Vigneaud et al., *J. Am. Chem. Soc.*, vol. 75 (1953) at 4880.

The compounds of this invention can be employed in mixtures with conventional excipients, i.e., physiologically and pharmaceutically acceptable organic or inorganic carriers suitable for parenteral or other application, provided that the carriers do not interact deleteriously with the active compounds.

Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing the osmotic pressure, buffers, coloring, flavoring and/or aromatic substances, which do not deleteriously interact with the active compounds.

For parenteral or intranasal application, solutions, preferably aqueous solutions, as well as suspensions, emulsions or implants, including suppositories, are particularly suitable. Ampoules are convenient unit dosages.

For enteral application, particularly suitable are tablets, dragrees, or capsules, having talc and/or a carbohydrate carrier or binder or the like, the carrier preferably being lactose and/or corn starch and/or potato starch. A syrup, elixir or the like can be used, wherein a sweetened vehicle is employed. Sustained release compositions can be formulated, including those wherein the active compound is protected with differentially degradable coatings, e.g., by microencapsulation, multiple coatings, etc.

The compounds of the General Formula are generally administered to animals, including but not limited to mammals, e.g, livestock, household pets, humans, cattle, cats and dogs. A diuretically effective daily dosage of the active compounds can be administered parenterally in a single dosage or as divided dosages throughout the day.

Parenteral or intranasal administration is preferred. The compounds of this invention are particularly valuable in the treatment of humans afflicted with water retention of any etiology. In this regard, they can be adminstered in substantially the same manner as the known compounds oxytocin and vasopressin, to achieve their physiological effects.

It will be appreciated that the actual preferred amounts of active compounds used will vary according to the specific compound being utilized, the particular compositions formulated, the mode of application, and the particular organisms being treated. Optimal application rates under/in a given set of conditions can be ascertained by those skilled in the art of using conventional dosage determination tests in view of the above guidelines.

DESCRIPTION OF PREFERRED EMBODIMENTS

Preferred antidiuretic antagonists of Group A are those wherein:
(a) X is D-Phe;
(b) X is D-Tyr(R) and R is methyl, ethyl, propyl or butyl;
(c) Y is Gln, including each of (a)-(b);
(d) Y is Ile, including each of (a)-(b);
(e) Y is Val, including each of (a)-(b);
(f) Z is Arg, including each of (a)-(e);
(g) Q is $NHCH_2CH_2OH$, including each of (a)-(f);
(h) Q is $NH(CH_2)_4NH_2$, including each of (a)-(f);
(i) Q is NHMe, including each of (a)-(f);
(j) Q is NHBu-n, including each of (a)-(f) and
(k) n is 5, including each of (a)-(j).

Most preferred compounds of Group A are those wherein n is 5, X is D-Phe or D-Tyr(Et), Y is Ile, Z is Arg and Q is $NH(CH_2)_2OH$.

Preferred compounds of Group B are those wherein:
(a) X is D-Phe;
(b) X is D-Tyr(R) and R is methyl, ethyl, propyl or butyl;
(c) X is D-Ile;
(d) n is 5, including each of (a)-(c);
(e) Y is Val, including each of (a)-(d);
(f) Y is Ile, including each of (a)-(d);
(g) Y is Gln, including each of (a)-(d);
(h) Z is Arg, including each of (a)-(g);
(i) M is Gly, including each of (a)-(h);
(j) M is Ala, including each of (a)-(h);
(k) M is Arg, including each of (a)-(h);
(l) P is NHMe, including each of (a)-(k);

(m) P is NHCH$_2$CH$_2$NH$_2$, including each of (a)–(k) and (n) P is NHCH$_2$CH$_2$OH, including each of (a)–(k).

Most preferred compounds of Group B are those wherein n is 5; X is D-Phe or D-Tyr(Et); Y is Ile; Z is Arg; M is Ala, Arg or Gly and P is NHMe, NHCH$_2$CH$_2$NH$_2$ or NHCH$_2$CH$_2$OH.

Preferred compounds of Group C are those wherein:
(a) n is 5;
(b) X is D-Phe, including (a);
(c) Y is Ile, including each of (a)–(b);
(d) Z is Arg, including each of (a)–(c);
(e) M is Gly, including each of (a)–(d) and
(f) A is Gly, including each of (a)–(d)
(f) P' is NH$_2$, including (a)–(f).

A most preferred compound of Group C is [1-(beta-mercapto-beta,beta-cyclopentamethylenepropionic acid), 2-D-phenylalanine, 4-isoleucine, 9-glycine]-arginine vasporessinyl-glycinamide.

Preferred compounds of Group D are those wherein:
(a) n is 5;
(b) Y is Ile, including (a);
(c) Z is Arg, including each of (a)–(b) and
(d) Q is NHCH$_2$CH$_2$NH$_2$, including each of (a)–(c).

A most preferred compound of Group D is [1-(beta-mercapto-beta,beta-cyclopentamethylenepropionic acid), 2-D-tyrosine, 4-isoleucine, 8-arginine-N-(beta-amino)ethylamine, 9-desglycinamide]vasopressin.

Without further elaboration, it it believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Chloromethylated resin (Bio-Rad Bio-Beads SX-1) was esterified by the procedure of Gisin, *Helv. Chim. Acta.*, vol. 56 (1973) at 1476 with Boc-Gly, for example, until 0.47 mmol./g. and ~0.64 mmol/g were incorporated. Amino acid derivatives, including Boc-Tyr(Me) (R$_f$(A) 0.7, R$_f$(B) 0.8) were supplied by Bachem or synthesized.

Triethylamine (TEA) and N-methylmorpholine (NMM) were distilled from ninhydrin. Ethylene diamine (ED) and n-butylamine were distilled from sodium. Ethanolamine was freshly distilled.

Acetic acid used as the HCl-acetic acid cleavage reagent was heated under reflux with boron triacetate and distilled from the reagent. Dimethylformamide (DMF) was distilled under reduced pressure immediately before use. Methanol was dried with magnesium methoxide and distilled. Other solvents and reagents were analytical grade.

Thin layer chromatography (TLC) was done on silica gel plates (0.25 mm, Brinkmann Silplate) using the following solvent systems: A. cyclohexane-chloroform-acetic acid (2:8:1 v/v); B. propan-1-ol-ammonia (34%) (2:1 v/v); C. ethanol (95%)-ammonia (34%) (3:1 v/v); D. chloroform-methanol (7:3 v/v); E. butan-1-ol-acetic acid-water (4:1:5 v/v, upper phase); F. butan-1-ol-acetic acid-water-pyridine (15:3:3:10 v/v). The applied loadings were 10–50 micrograms. The minimum length of the chromatograms was 10 cm. Chloroplatinate reagent and iodine vapor were used for development of the chromatograms.

Amino acid analysis of the peptides was done by the method of Spackman et al., *Anal. Chem.*, vol. 30 (1958) at 1190, in which peptide samples weighing about 0.5 mg were hydrolyzed with constant boiling hydrochloric acid (400 microliters) in evacuated and sealed ampoules for 18 h at 120° C. The analyses were performed using a Beckman Automatic Amino Acid Analyzer, Model 121. Molar ratios were referred to Gly=1.00. Elemental analyses were performed by Galbraith Laboratories, Inc., Knoxville, Tenn. The analytical results for the elements indicated by their respective symbols were within ±0.4% of theoretical values. Optical rotations were measured with a Bellingham Stanley, Ltd., Model A polarimeter, type p1.

EXAMPLE 1 beta-(S-Benzylmercapto)-beta,beta-cyclopentamethylenepropionyl-Tyr(Me)-Phe-Gln-Asn-Cys(Bzl)-Pro-Arg(Tos)-Gly-NH$_2$ (a) Combination of Solid Phase and Solution Methods.

Boc-Tyr(Me)-Phe-Gln-Asn-Cys(Bzl)-Pro-Arg(Tos)-Gly-NH$_2$, prepared by the method of Bankowski et al., *J. Med. Chem.*, vol. 21 (1978) at 850 (319 mg, 0.26 mmol), was dissolved in CF$_3$COOH (6.5 ml) and stirred at room temperature for 40 mins. Cold ether (20 ml) was added to produce a precipitate, which was filtered and washed with ether (5×10 ml). The product was dried in vacuo over sodium hydroxide pellets. This material (318.5 mg) was dissolved in DMF (0.8 ml), to which was added N-methylmorpholine (10 microliters). The resulting solution had a pH of 7–8, measured with moist pH paper. After this neutralized solution was stirred at room temperature for 30 mins, a solution of p-nitrophenyl beta-(S-benzylmercapto)-beta,beta-cyclopentamethylenepropionate, Nestor et al., *J. Med. Chem.*, vol. 18 (1975) at 284, (445 mg, 1.155 mmol in 0.4 ml of DMF) was added. The reaction mixture was stirred at room temperature. After 72 hours' stirring, TLC analysis using system D showed that the reaction mixture still contained a trace of the free octapeptide amide. N-Hydroxybenzotriazole monohydrate, Konig et al., *Chem. Ber.*, vol. 103 (1970) at 788, (39.3 mg, 0.26 mmol) was added. Coupling was complete within 5 hours. The precipitate was filtered, washed with cold ethyl acetate (4×10 ml) and dried in vacuo. The crude product (339 mg) was twice reprecipitated from DMF-methanol to give the acylpeptide amide (295.2 mg, 77.3%): mp 209°–211° C., $[\alpha]_D^{24} = -43.6°$ (c 0.5, DMF); R$_f$(E) 0.45, R$_f$(F) 0.63 Anal. (C$_{73}$H$_{94}$O$_{14}$N$_{14}$S$_3$) C, H, N.

(b) Total Synthesis on Resin.

Boc-Tyr(Me)-Phe-Gln-Asn-Cys(Bzl)-Pro-Arg(Tos)-Gly-resin (1.11 g, 0.4 mmol prepared from Boc-Gly-resin using solid phase methodology) was converted to the acyloctapeptide resin (1.167 g, weight gain 57 mg, 97.6% of theory) in one cycle of deprotection, neutralization and coupling with p-nitrophenyl beta-(S-benzyl-mercapto)-beta,beta-cyclopentamethylenepropionate, see Nestor, supra. The resin was ammonolyzed, Manning, *J. Am. Chem. Soc.*, vol. 90 (1968) at 1348. The product was extracted with DMF. After the solvent was evaporated in vacuo, the residue was precipitated by addition of water. The crude product (410 mg) was twice reprecipitated from DMF-ethanol to give the acyloctapeptide (302 mg, 50.7% based upon initial glycine content of the resin); mp 206°–208° C. (decomp);

$R_f(E)$ 0.45; $R_f(F)$ 0.63; $[\alpha]_D^{24} = -43.1°$ (c 1, DMF). Anal. ($C_{73}H_{94}N_{14}O_{14}S_3$) C, H, N.

Amino acid analysis: Tyr, 0.79; Phe, 1.01; Glu, 1.03; Asp, 1.04; Cys(Bzl), 0.97; Pro, 1.03; Arg, 0.99; Gly, 1.00; $NH_3$, 2.95.

EXAMPLE 2 beta-(S-Benzylmercapto)-beta,beta-cyclopentamethylenepropionyl-Tyr(Bzl)-Phe-Gln-Asn-Cys(Bzl)-Pro-Arg(Tos)-Gly-$NH_2$ Boc-Tyr(Bzl)-Phe-Gln-Asn-Cys(Bzl)-Pro-Arg(Tos)-Gly-resin (1.46 g, 0.5 mmol) was converted to the acyloctapeptide resin (1.55 g, weight gain 70 mg, 95.9% of theory) as in Example 1 by one cycle of deprotection, neutralization and coupling with p-nitrophenyl beta-(S-benzylmercapto)-beta,beta-cyclopentamethylenepropionate. The product obtained by ammonolysis of the resin was extracted with DMF. The solvent was evaporated in vacuo and the residue was precipitated by addition of water. The crude product (723 mg) was reprecipitated from DMF-ethanol and DMF-2% aqueous AcOH. Yield: 488 mg (62.4% based on initial Gly content on the resin); mp 183°-185° C.; $R_f(E)$ 0.38; $R_f(D)$ 0.41; $[\alpha]_D^{23} = -23.9°$ (c 1, DMF). Anal. ($C_{79}H_{98}N_{14}O_{14}S_3$) C, H, N.

Amino acid analysis: Tyr, 0.97; Phe, 1.02; Glu, 1.05; Asp, 1.01; Cys(Bzl), 0.98; Pro, 1.04; Arg, 0.98; Gly, 1.00; $NH_3$.

EXAMPLE 3

[1-(beta-Mercapto-beta,beta-cyclopentamethylenepropionic acid), 2-(O-methyl)tyrosine]-arginine vasopressin (a) From Nonapeptide Amide A solution of the protected nonapeptide amide, prepared as in Example 1, (170 mg, 0.114 mmol) in 400 ml of ammonia (dried over sodium and redistilled) was stirred at the boiling point with sodium from a stick of the metal, contained in a small bore glass tube until a light blue color persisted in the solution for 30 sec, in accordance with du Vigneaud, *J. Am. Chem. Soc.*, vol. 76 (1954) at 3115. Dry glacial acetic acid (0.4 ml) was added to discharge the color. The solution was evaporated. A solution of the residue in aqueous acetic acid (0.2%, 800 ml), was treated with 2M ammonium hydroxide solution to give a solution of pH 7.5. To this stirred solution was added gradually an excess of a solution of potassium ferricyanide (0.01M, 11.4 ml), Hope et al., *J. Biol. Chem.*, vol. 237 (1962) at 1563. The yellow solution was stirred for 90 min more and for 1 h with anion-exchange resin (BioRad AG-3, Cl⁻ form, 10 g damp weight). The suspension was filtered slowly through a bed of resin (80 g damp weight). The resin bed was washed with 300 ml of aqueous acetic acid and the combined filtrate and washings were lyophilized. The resulting powder (1386 mg) was desalted on a Sephadex G-15 column (110×2.7 cm) and eluted with aqueous acetic acid (50%) at a flow rate of 4 ml/h by the technique of Manning et al., *J. Chromatog.*, vol. 38 (1968) at 396. The eluate was fractionated and monitored for absorbance at 280 nm. The fractions comprising the major peak were pooled and lyophilized. The residue (55.5 mg) was further subjected to gel filtration on a Sephadex G-15 column (100×1.5 cm) and eluted with aqueous acetic acid (0.2M) at a flow rate of 2.5 ml/h. The peptide was eluted in a single peak (absorbance 280 nm). Lyophilization of the pertinent fractions yielded the vasopressin analog (49 mg, 37.3%); $R_f(E)$ 0.19; $R_f(F)$ 0.30; $[\alpha]_D^{22} = -59.6°$ (c 0.19, 1M AcOH).

Amino acid analysis: Tyr 0.81; Phe, 1.01; Glu, 1.04; Asp, 0.98; Pro, 1.04; Arg, 0.95; Gly, 1.00; $NH_3$ 3.10. Analysis following performic acid oxidation prior to hydrolysis according to Moore, *J. Biol. Chem.*, vol. 238 (1963) at 235, gave a Cys-($O_3$H)-Gly ratio of 1.03:1.00.

(b) From Acyloctapeptide.

Treatment of the acyloctapeptide (160 mg, 0.107 mmol) as described in Example 3(a) yielded the analog (64 mg, 51.7%), which was indistinguishable from the foregoing preparation by TLC: $[\alpha]_D^{23} = -59.1°$ (c 0.5, 1M AcOH).

Amino acid analysis: Tyr, 0.80; Phe, 1.02; Glu, 1.02; Asp, 0.98; Pro, 1.03; Arg, 0.96; Gly, 1.00; $NH_3$, 3.05. Analysis following performic acid oxidation prior to hydrolysis gave a Cys-($O_3$H)-Gly ratio of 1.02:1.00.

EXAMPLE 4

[1-(beta-Mercapto-beta,beta-cyclopentamethylenepropionic acid), 2-substituted, 4-substituted, 9-desglycine]-arginine vasopressin The compounds were made in the same manner as the compounds of Examples 1-3, starting from Boc-Arg(Tos) resin, except that one fewer cycle of deprotection, neutralization and coupling was employed. Protected intermediates for each analog were obtained. Coupling with beta-(S-benzylmercapto)-beta,beta-cyclopentamethylenepropionate was done in accordance with Nestor, supra. The cyclopentamethylene compound can also be made using the technique of Yim et al., *Int. J. Peptide Protein Res.*, vol. 21 (1983), at 568.

Each precursor was deblocked with sodium in liquid ammonia to produce a sulfhydryl compound. The latter compounds were oxidatively cyclized with potassium ferricyanide, as in the preceding Examples. The analogs were desalted and purified by gel filtration on Sephadex G-15 by a two-step procedure using 50% acetic acid and 0.2M acetic acid, respectively, as eluants. The purity and identity of each analog was ascertained by thin-layer chromatography in three different solvent systems, BAW I (butan-1-ol-acetic acid, water 4:1:1 v/v), BAWP (butan-1-ol-acetic acid-water-pyridine 15:3:3:10 v/v) and BAW II (butan-1-ol-acetic acid-water 4:1:5 v/v, upper phase) with the following results:

| Compound | $R_f$ | | |
|---|---|---|---|
| | BAW I | BAWP | BAW II |
| desGly⁹AVP | 0.04 | 0.27 | 0.23 |
| desGly⁹d(CH₂)₅[D-Phe²]VAVP | 0.39 | 0.59 | 0.39 |
| desGly⁹d(CH₂)₅[D-Phe²,Ile⁴]AVP | 0.41 | 0.63 | 0.40 |
| desGly⁹d(CH₂)₅[D-Tyr(Et)²]VAVP | 0.39 | 0.60 | 0.38 |
| desGly⁹d(CH₂)₅[Tyr(Et)²]VAVP | 0.41 | 0.65 | 0.41 |
| desGly⁹d(CH₂)₅[Tyr(Me)²]AVP | 0.21 | 0.51 | 0.33 |

EXAMPLE 5

[1-(beta-Mercapto-beta,beta-cyclopentamethylenepropionic acid), 9-desglycinamide]-arginine vasopressin This compound, desGly($NH_2$)⁹d($CH_2$)₅AVP, was obtained from the protected precursor, beta-(S-benzylmercapto)-beta,beta-cyclopentamethylenepropionyl-Tyr-(Bzl)Phe-Gln-Asn-Cys(Bzl)Pro-Arg(Tos)Bzl, which was synthesized in solution by the stepwise procedure of Bodansky et al., *J. Am. Chem. Soc.*, vol. 81 (1959) at 1173, starting from Boc-Arg(Tos)Bzl. Following cleavage of the Boc group with 1N HCl/HOAc and neutralization with triethylamine, successive couplings with Boc-Pro and Boc-Cys(Bzl) were performed, in the presence of dicyclohexylcarbodiimide (DCC) and hydroxybenzotriazole (HOBT) in accordance with Sheehan et al., *J. Am. Chem. Soc.*, vol. 77 (1955) at 1067 and Konig et al., *Chem. Ber.*, vol. 103 (1970) at 788.

The Asn and Gln residues were incorporated as corresponding Boc nitrophenyl esters. 1-Cyclohexyl-3-[2-morpholinyl-(5)-carbodiimide] (CMCD) and HOBT were used for coupling of Boc-Phe and Boc-Tyr(Bzl) to give the protected heptapeptide benzyl ester. Coupling with p-nitrophenyl beta-(S-benzylmercapto)-beta,beta-cyclopentamethylene propionate, by the procedure of Nestor et al., supra, yielded the required protected intermediate. Deblocking with sodium in liquid ammonia and purification were carried out as above.

Purity of the compound was determined as above, with the following $R_f$ values:

| | |
|---|---|
| BAW I: | 0.07 |
| BAWP: | 0.18 |
| BAW II: | 023 |

EXAMPLE 6

(a)

[1-(beta-Mercapto-beta,beta-cyclopentamethylenepropionate acid), 2-D-phenylalanine, 4-valine, 9-desglycineamide]-arginine vasopressin The compound, desGly(NH$_2$)$^9$d(CH$_2$)$_5$[D-Phe$^2$]-VAVP, was obtained from the protected precursor, beta-S-(benzylmercapto)-beta,beta-cyclopentamethylenepropionyl-D-Phe-Phe-Val-Asn-Cys(Bzl)-Pro-Arg(Tos)Bzl, which was synthesized in solution, starting from Boc-Phe-Val-Asn-Cys(Bzl)-Pro-Arg(Tos)-Bzl, prepared by custom synthesis at Alpha Biomedicals, Inc., San Carlos, Calif., except that cleavage of the Boc groups was done by trifluoroacetic acid, Boc-D-Phe was used instead of Boc-Tyr(Bzl) and coupling of beta-(S-benzylmercapto)-beta,beta-cyclopentamethylenepropionic acid was mediated by DCC and HOBT to give the required protected intermediate.

The product was characterized by TLC with the following $R_f$ values:

| | |
|---|---|
| BAW I: | 0.40 |
| BAWP | 0.46 |
| BAW II | 0.39 |

(b) Other compounds of this type were made by acidolytic cleavage of the appropriate Arg(Tos) peptide resin as described in Example 7(a). The compounds were characterized by TLC:

| Compound | $R_f$ BAW I | BAW II | BAWP |
|---|---|---|---|
| desGly(NH$_2$)$^9$d(CH$_2$)$_5$[D-Tyr(Et)$^2$]VAVP | 0.30 | 0.38 | 0.50 |
| desGly(NH$_2$)$^9$d(CH$_2$)$_5$[D-Phe$^2$,Ile$^4$]AVP | 0.45 | 0.38 | 0.45 |
| desGly(NH$_2$)$^9$d(CH$_2$)$_5$[Tyr(Me)$^2$]AVP | 0.16 | 0.25 | 0.30 |

EXAMPLE 7

[1-(beta-Mercapto-beta,beta-cyclopentamethylenepropionic acid), 2-D-phenylalanine, 4-isoleucine, 9-desamido]-arginine vasopressin A compound of the formula d(CH$_2$)$_5$[D-Phe$^2$, Ile$^4$-]AVP acid was obtained from a protected precursor, beta-S-(benzylmercapto)-beta,beta-cyclopentamethylenepropionyl-D-Phe-Phe-Ile-Asn-Cys(Bzl)-Pro-Arg(Tos)-Gly, which was synthesized by the solid phase method, starting from Boc-resin as in the foregoing examples, except that the partially protected precursor was cleaved from the resin by acidolysis with hydrogen bromide in trifluoroacetic acid containing anisole by the method of Walter et al., *J. Med. Chem.*, vol. 19 (1976) at 376. After evaporation of the trifluoroacetic acid, the product was obtained by precipitation from an acetic acid solution with diethyl ether. The intermediate was deblocked with sodium in liquid ammonia, reoxidized, lyophilized and purified as in the foregoing examples. The product was characterized by TLC, with the following values:

| | |
|---|---|
| BAW I | 0.15 |
| BAWP | 0.39 |
| BAW II | 0.29 |

EXAMPLE 8

Antagonism to the vasopressor response was estimated in accordance with Dyckes et al., *J. Med. Chem.*, vol. 17 (1974) at 969. The values are expressed as pA$_2$ values, defined as in Schild et al., *Br. J. Pharmacol.*, vol. 2 (1947) at 189.

Activity as antidiuretic agonists was determined by intravenous injection of the compounds being evaluated in ethanol-anesthesized water-loaded rats in accordance with Sawyer, *Endocrinology*, vol. 63 (1958) at 694. Antagonism of the antidiuretic response to subsequent injections of arginine vasopressin was tested by the method of Sawyer et al., *Science*, vol. 212 (1981) at 49.

Antagonistic potencies were determined and expressed as "effective doses" and pA$_2$ values. The "effective dose" is defined as the dose (in nanomoles per kilogram) that reduces the response seen from 2x units of agonist injected 20 min after the dose of antagonist to the response with 1x units of agonist. Estimated in vivo "pA$_2$" values represent the negative logarithms of the effective doses, divided by the estimated volume of distribution (67 ml/kg). Results are given in Table 1.

TABLE 1

| Compound | Agonistic Activities units/mg | | Anti-ADH nmoles/kg | | Anti-VP nmoles/kg | |
|---|---|---|---|---|---|---|
| | ADH | VP | ED | pA$_2$ | ED | pA$_2$ |
| AVP | 330 ± 23 | 382 ± 5 | — | — | — | — |
| AVP-acid[a,b] | 4.7 ± 0.6 | <0.03 | — | — | — | — |

TABLE 1-continued

| Compound | Agonistic Activities units/mg | | Anti-ADH nmoles/kg | | Anti-VP nmoles/kg | |
|---|---|---|---|---|---|---|
| | ADH | VP | ED | pA$_2$ | ED | pA$_2$ |
| desGly$^9$AVP | 164 ± 4 | <0.05+ | — | — | 68 ± 16 | 6.09 ± 0.10 |
| desGly$^9$(NH$_2$)AVP$^c$ | 5.6 ± 1.1 | ~0.02+ | — | — | — | — |
| d(CH$_2$)$_5$AVP | 0.03 ± 0.01 | — | — | — | 0.56 ± 0.11 | 8.16 ± 0.09 |
| desGly$^9$d(CH$_2$)$_5$AVP | ~0.003+ | — | — | — | 0.27 ± 0.04 | 8.40 ± 0.06 |
| desGly(NH$_2$)$^9$d(CH$_2$)$_5$AVP | 0.04 ± 0.01 | — | — | — | 0.73 ± 0.07 | 7.88 ± 0.06 |
| d(CH$_2$)$_5$[D-Phe$^2$]VAVP | weak+ | — | 0.67 ± 0.13 | 8.06 ± 0.09 | 0.58 ± 0.04 | 8.06 ± 0.03 |
| desGly$^9$d(CH$_2$)$_5$[D-Phe$^2$]VAVP | — | — | 0.58 ± 0.11 | 8.09 ± 0.08 | 0.47 ± 0.04 | 8.15 ± 0.03 |
| desGly(NH$_2$)$^9$d(CH$_2$)$_5$—[D-Phe$^2$]VAVP | — | — | 1.3 ± 0.4 | 7.75 ± 0.11 | 0.80 ± 0.08 | 7.93 ± 0.05 |
| d(CH$_2$)$_5$[Tyr(Et)]$^2$VAVP | ~0.03+ | — | 1.9 ± 0.2 | 7.57 ± 0.06 | 0.49 ± 0.11 | 8.16 ± 0.09 |
| desGly$^9$d(CH$_2$)$_5$[Tyr(Et)$^2$]VAVP | — | — | 1.0 ± 0.2 | 7.89 ± 0.09 | 0.45 ± 0.02 | 8.18 ± 0.02 |
| d(CH$_2$)$_5$[D-Tyr(Et)$^2$]VAVP | weak+ | — | 1.1 ± 0.2 | 7.81 ± 0.07 | 0.45 ± 0.11 | 8.22 ± 0.12 |
| desGly$^9$d(CH$_2$)$_5$[D-Tyr(Et)$^2$]—VAVP | — | — | 1.5 ± 0.3 | 7.69 ± 0.08 | 0.45 ± 0.04 | 8.17 ± 0.04 |
| d(CH$_2$)$_5$[D-Phe$^2$,Ile$^4$]AVP | — | — | 0.46 ± 0.07 | 8.24 ± 0.08 | 0.99 ± 0.12 | 7.86 ± 0.05 |
| desGly$^9$d(CH$_2$)$_5$—[D-Phe$^2$,Ile$^4$]AVP | — | — | 0.66 ± 0.17 | 8.05 ± 0.09 | 1.0 ± 0.1 | 7.84 ± 0.03 |
| d(CH$_2$)$_5$[D-Phe$^2$,Ile$^4$]AVP acid | — | — | 6.4 ± 2.1 | 7.11 ± 0.11 | 8.0 ± 1.3 | 6.94 ± 0.08 |
| desGly(NH$_2$)$^9$d(CH$_2$)$_5$—[D-Phe$^2$, Ile$^4$]AVP | — | — | 4.6 ± 1.2 | 7.20 ± 0.10 | 14 ± 2 | 6.74 ± 0.08 |
| desGly(NH$_2$)$^9$d(CH$_2$)$_5$—[D-Tyr(Et)$^2$]VAVP | — | — | 1.1 ± 0.08 | 7.78 ± 0.03 | 1.2 ± 0.04 | 7.77 ± 0.02 |
| desGly$^9$d(CH$_2$)$_5$[Tyr(Me)$^2$]AVP | ~0.01+ | — | ~54+ | ~6.1 | 0.27 ± 0.06 | 8.44 ± 0.10 |
| desGly(NH$_2$)$^9$d(CH$_2$)$_5$—[Tyr(Me)$^2$]AVP | ~0.0005+ | — | ~280 | ~5.4 | 0.23 ± 0.02 | 8.46 ± 0.05 |

$^a$AVP-acid was purchased from Bachem, Inc.
$^b$This compound was originally reported as being an ADH antagonist in vitro and in vivo, Dousa et al., supra. These results show it is an antidiuretic agonist in vivo.
$^c$Originally obtained by tryptic cleavage of AVP, du Vigneaud et al., J. Am. Chem. Soc., vol. 75 (1953) at 4880.
+ Compounds showed weak partial agonistic activities in these assays, in a way not clearly related to dose.

EXAMPLE 9

(a)

[1-(beta-Mercapto-beta,beta-cyclopentamethylenepropionic acid), 2-D-phenylalanine, 4-isoleucine, 9-substituted]-arginine vasopressin Compounds of this series were prepared as in the foregoing examples, except that an amino acid, other than glycine, was attached to the resin in the first cycle of the synthesis. Compounds of this series can also be synthesized by the 8+1 coupling in solution, described in Example 9(b). The compounds obtained were of the formula d(CH$_2$)$_5$[D-Phe$^2$, Ile$^4$, Q$^9$]AVP and were characterized by TLC as in the foregoing examples. The following results were obtained:

| Q | R$_f$ | | |
|---|---|---|---|
| | BAW I | BAWP | BAW II |
| Arg(NH$_2$) | 0.11 | 0.37 | 0.27 |
| Ser(NH$_2$) | 0.39 | 0.59 | 0.35 |
| Ala(NH$_2$) | 0.41 | 0.64 | 0.37 |
| D-Ala(NH$_2$) | 0.42 | 0.64 | 0.37 |
| Orn(NH$_2$) | 0.01 | 0.25 | 0.19 |
| Ile(NH$_2$) | 0.51 | 0.75 | 0.40 |
| Val(NH$_2$) | 0.47 | 0.72 | 0.44 |
| Thr(NH$_2$) | 0.46 | 0.76 | 0.35 |
| Phe(NH$_2$) | 0.51 | 0.82 | 0.53 |
| Pro(NH$_2$) | 0.29 | 0.62 | 0.31 |
| Tyr(NH$_2$) | 0.49 | 0.70 | 0.40 |

(b)

[1-(beta-Mercapto-beta,beta-cyclopentamethylenepropionic acid, 2-O-methyltyrosine, 9-alaninamide]-arginine vasopressin by combination of solid phase and solution methods, 8+1 coupling A compound represented by the formula d(CH$_2$)$_5$[Tyr(Me)$^2$, AlaNH$_2$9]AVP was synthesized from a protected peptidyl resin, beta-(S-benzylmercapto)-beta,beta-cyclopentamethylenepropionyl-Tyr(Me)-Phe-Gln-Asn-Cys(Bzl)-Pro-Arg(Tos)-resin (14.0 g), suspended in 100 ml of trifluoroacetic acid (TFA) containing 20 ml of anisole. Hydrogen bromide was bubbled through the suspension for 30 min at room temperature in accordance with Walter et al., supra, at 376. The resulting supernatant was collected and the resin was resuspended in 100 ml of 1:1 TFA:CH$_2$Cl$_2$ and hydrogen bromide was bubbled through the suspension for 30 min more. The supernatants were combined, evaporated to dryness and triturated with ether. Recrystallization from acetic acid/ether gave 3.42 g of the protected octapeptide, beta-(S-benzylmercapto)-beta,beta-cyclopentamethylenepropionyl-Tyr(Me)-Phe-Gln-Asn-Cys(Bzl)-Pro-Arg(Tos), mp 180°–186° C., $[\alpha]_D^{23} = -20.8°$ (c=0.5, DMF).

Thin layer chromatography gave the following R$_f$ values

| BAW II | 0.56 |
|---|---|
| BAWP | 0.68 |
| BAW I | 0.48 |

An aliquot of the thus-prepared octapeptide (367 mg, 0.25 mmol) and 77 mg (0.5 mmol) of N-hydroxybenzotriazole (HOBT) was dissolved in 2.0 ml of DMF. Alaninamide hydrochloride (94 mg, 0.75 mmol) was added and the pH was brought to about 7.5 with triethylamine (50 microliters). The resulting mixture was cooled to 0° C. and dicyclohexyl carbodiimide (52 mg, 0.25 mmol in 0.5 ml of DMF) was added. To this mixture was added about 30 ml of triethylamine to maintain pH at about 7.5. The resulting mixture was stirred overnight. Completion of the reaction was demonstrated by TLC. The product was isolated by precipitation from aqueous DMF and reprecipitated from DMF:ethanol:e- ther. The yield was 320 mg (84.2%), mp. 185°–189° C., $[\alpha]_D^{24} = -31.7°$ (c=1.0, DMF).

The product was characterized by TLC and had the following $R_f$ values:

| | |
|---|---|
| BAW II | 0.54 |
| BAW I | 0.46 |
| BAWP | 0.80 |

The protected precursor (200 mg) was reduced with sodium in liquid ammonia, reoxidized, deionized and purified as described above to give the desired 9-alaninamide free peptide, $[\alpha]_D^{23} = -76.9°$ (c=0.3, 1M HOAc)

Characterization by TLC gave the following $R_f$ values:

| | |
|---|---|
| BAW I | 0.27 |
| BAWP | 0.48 |
| BAW II | 0.26 |

(c) Evaluation

The compounds were evaluated as in Example 8 to determine effective doses as antagonists of the antidiuretic action of arginine vasopressin. Results are presented in Table 2 and show that the indicated modifications at the 9-position produce compounds which antagonize the antidiuretic and/or vasopressor action of AVP.

TABLE 2

| Q in d(CH$_2$)$_5$D-Phe$^2$,Ile$^4$Q$^9$AVP | Anti-ADH Potency | | Anti-VP Potency | | ED ratio |
|---|---|---|---|---|---|
| | ED | pA$_2$ | ED | pA$_2$ | |
| Ala(NH$_2$) | 0.31 ± 0.07 | 8.38 ± 0.13 | 1.5 ± 0.1 | 7.67 ± 0.04 | 4.8 |
| Orn(NH$_2$) | 0.46 ± 0.09 | 8.18 ± 0.09 | 1.1 ± 0.1 | 7.80 ± 0.05 | 2.4 |
| Ser(NH$_2$) | 0.55 ± 0.09 | 8.10 ± 0.07 | 0.54 ± 0.09 | 8.10 ± 0.08 | 1.0 |
| Val(NH$_2$) | 0.57 ± 0.14 | 8.11 ± 0.11 | 1.6 ± 0.4 | 7.66 ± 0.10 | 2.8 |
| Arg(NH$_2$) | 0.67 ± 0.15 | 8.05 ± 0.11 | 0.55 ± 0.09 | 8.11 ± 0.07 | 0.82 |
| Phe(NH$_2$) | 1.5 ± 0.3 | 7.69 ± 0.09 | 3.8 ± 0.9 | 7.28 ± 0.11 | 2.5 |
| Ile(NH$_2$) | 1.9 ± 0.5 | 7.58 ± 0.11 | 6.3 ± 0.8 | 7.04 ± 0.05 | 3.3 |
| Thr(NH$_2$) | 2.7 ± 0.8 | 7.39 ± 0.04 | 1.7 ± 0.4 | 7.64 ± 0.11 | 0.63 |
| D-Ala(NH$_2$)* | 2.9 ± 0.4 | 7.38 ± 0.08 | 1.9 ± 0.2 | 7.55 ± 0.05 | 0.66 |
| Pro(NH$_2$)* | 4.4 ± 0.4 | 7.19 ± 0.04 | 5.7 ± 1.7 | 7.12 ± 0.11 | 1.3 |
| Tyr(NH$_2$) | 0.95 ± 0.15 | 7.85 ± 0.06 | 3.7 ± 0.4 | 7.27 ± 0.05 | 3.9 |

*These peptides produced inconsistent weak and transient antidiuretic effects, in a way not clearly related to dose.

The compound of Example 9(b) had the following activity:
Anti-VP: ED, 0.13±0.03; pA$_2$, 8.74±0.08
Anti-ADH: ED, about 77 (mixed); pA$_2$, about 6.0

EXAMPLE 10

(a)
[1-(beta)-Mercapto-beta,beta-cyclopentamethylenepropionic acid), 2-substituted, 4-substituted, 9-desglycinamide]-arginine vasopressin derivatives Desglycinamide compounds are made as in Example 4, starting from Boc-Arg(Tos)-resin. The terminal arginine function is cleaved from the resin using a cleaving agent corresponding to QH in the structural formulas. Results of TLC and pharmacological evaluation are given in Tables 3 and 4, respectively.

When Q is NH$_2$, cleavage from the resin is done with ammonia, in accordance with Manning et al., supra.

When Q is —NH(CH$_2$)$_p$NH$_2$, NH(CH$_2$)$_q$OH or alkNH$_2$, the product is cleaved from the resin by the method of Glass et al., supra., using an alkylene diamine, an alkanolamine or an alkylamine, respectively.

(i) Cleavage with ethanolamine

Protected peptidyl resin, beta-(S-benzylmercapto)-beta,beta-cyclopentamethylenepropionyl-D-Tyr(Et)-Phe-Ile-Asn-Cys(Bzl)-Pro-Arg(Tos)-resin (3 g, about 0.75 mmol) was suspended in 15 ml of anhydrous methanol and 15 ml of freshly-distilled ethanolamine (bp above 171° C.) and stirred at room temperature for four days. Following removal of the solvents, the residue was extracted with hot DMF and reprecipitated with 1 L of water and with DMF/ether to give 640 mg of product. The uncyclized product was characterized by TLC, as follows:

| | |
|---|---|
| BAW II | 0.82 |
| CHCl$_3$:MeOH (9:1) | 0.25 |

The product was deblocked cyclized and purified as described in the foregoing examples to give the free peptide, [1-(beta-mercapto-beta,beta-cyclopentamethylenepropionic acid), 2-D-(O-ethyl)tyrosine, 4-isoleucine, 8-arginine-N-(beta-hydroxy)ethylamide, 9-desglycinamide]-arginine vasopressin. The yield was 15.5 mg (13.4%).

(b)
[1-(beta-(Mercapto)-beta,beta-cyclopentamethylenepropionic acid), 2-substituted, 4-substituted, 9-modified]-arginine vasopressin Compounds are prepared as in Examples 1–3. A protected nonapeptide is cleaved from the resin with an agent, corresponding to QH in the formulas, by methods outlined in Example 10(a). Alternatively, the compounds can be made by 8+1 coupling in solution.

(i) Cleavage with methylamine

Protected peptidyl resin, beta-(S-benzylmercapto)-beta,beta-cyclopentamethylenepropionyl-D-Tyr(Et)-Phe-Val-Asn-Cys(Bzl)-Pro-Arg(Tos)-Gly-resin (3.02 g, 1 mmol), was suspended in 50 ml of dry methanol. Methylamine was bubbled through the suspension until the volume increased by about 10 ml. The flask was stoppered and stirred at room temperature for 72 h, after which solvents were removed by evaporation. The product was extracted with hot DMF (3×25 ml portions) and precipitated by addition of 1 L of water. The product weighed 2.53 g and was reprecipitated from DMF-ethanol and DMF-ethanol-ether to give 1.03 g (69.3%), of uncyclized peptide, mp 180°–182° C.

The intermediate (150 mg) was reduced with sodium in liquid ammonia, reoxidized, deionized and purified as above to give 45 mg (38.7%) of d(CH$_2$)$_5$[D-Tyr(Et)$^2$, Val$^4$, GlyNHMe$^9$]AVP.

(ii) Cleavage with n-butylamine

Protected peptidyl resin, beta-(S-benzylmercapto)-beta,beta-cyclopentamethylenepropionyl-Tyr(Me)-Phe-Gln-Asn-Cys(Bzl)-Pro-Arg(Tos)-Gly-resin (2.0 g), was suspended in 10 ml of anhydrous methanol and 20 ml of n-butylamine, freshly distilled from sodium, and the resulting mixture was stirred at room temperature for 4 days. The solvents were removed by evaporation. The residue was extracted with DMF. The product was precipitated from the DMF solution with water, dried and reprecipitated from DMF with ethanol/ether to give the protected intermediate, having the terminal sequence -Pro-Arg(Tos)-GlyNHC$_4$H$_9$-n, $[\alpha]_D^{24} = -34°$ (c=1, DMF).

The intermediate had the following R$_f$ by TLC:

| | |
|---|---|
| BAW II | 0.76 |
| BAWP | 0.88 |
| CHCl$_3$:MeOH (9:1) | 0.73 |

The intermediate (150 mg) was deblocked with sodium in liquid ammonia and purified as above to give 55 mg (48.3%) of the cyclized free peptide, d(CH$_2$)$_5$-[Tyr(Me)$^2$, GlyNHBu-n$^9$]AVP, $[\alpha]_D^{24} = -43.3°$ (c=0.3, 1N HOAc)

(iii)

[1-(beta-mercapto-beta,beta-cyclopentamethylenepropionic acid), 2-D-(O-ethyl)tyrosine, 4-valine, 9-beta-alanine-N-methylamide]-arginine vasopressin by 8+1 solution synthesis Protected acyloctapeptide, beta-(S-benzylmercapto)-beta,beta-cyclopentamethylenepropionyl-D-Tyr(Et)-Phe-Val-Asn-Cys(Bzl)-Pro-Arg(Tos) (442.1 mg, 0.3 mmol), obtained by cleavage of protected peptidyl resin with HBr/TFA as described in Example 9(b), was coupled with beta-alanine-N-methylamide hydrochloride (166.3 mg, 1.2 mmol), as described in Example 9(b) to give the protected intermediate, terminated with a beta-alanine-N-methylamide moiety. The product weighed 361.7 mg (50.1%), mp 195°–200° C.

TLC had the following R$_f$ values:

| | |
|---|---|
| CHCH$_3$:MeOH (9:1) | 0.73 |
| BAW II | 0.74 |
| BAWP | 0.79 |

The blocking groups were removed, after which the deblocked material was reoxidized, deionized and purified as above to give the free peptide in 35.4 mg (30.4%) yield. $[\alpha]_D^{28} = -51.3°$ (c=0.3, 1N HOAc).

(c)

[1-(beta-Mercapto-beta,beta-cyclopentamethylenepropionic acid), 2-D-phenylalanine, 4-isoleucine, 9-glycine]-arginine vasopressinyl glycinamide The compound is prepared as in Examples 1–3, starting from Boc-Gly-Gly-resin or a corresponding intermediate in solution. The cyclized protected intermediate is subjected to ammonolysis as in Example 3. This compound and related decapeptides could also be made by 9+1 coupling, similar to the procedure described in Example 9(b).

The products are characterized by TLC as in the foregoing examples. Pharmacological properties are evaluated as in Example 8. Results are given in Tables 3 and 4, respectively.

EXAMPLE 11

Oral Administration

The compound wherein n is 5, X is D-Phe, Y is Ile, Z is Arg and Q is NHCH$_2$CH$_2$NH$_2$ was administered orally in large doses to ethanol-anesthesized rats. Results among rats varied. In eight out of 12 rats, there was clear inhibition of antidiuretic responses to AVP, injected intravenously 30 min after the antagonist was given through an indwelling stomach tube in doses of 10–15 micrograms per rat (190–220 g body weight). Responses were reduced by 35±10%. The "effective" oral dosage is therefore about 75 nmoles/kg, compared to an effective intravenous dose of 0.55 nmoles/kg for this analog.

TABLE 3

| | R$_f$ | | |
|---|---|---|---|
| | BAW I | BAWP | BAW II |
| Compounds of Example 10(a) | | | |
| desGly(NH$_2$)$^9$d(CH$_2$)[D-Phe$^2$, Ile$^4$, Arg (NHCH$_2$CH$_2$OH)$^8$]VP | 0.29 | 0.72 | 0.36 |
| desGly(NH$_2$)$^9$d(CH$_2$)$_5$[D-Tyr(Et)$^2$, Ile$^4$, Arg(NHCH$_2$CH$_2$OH)$^8$]VP | 0.46 | 0.83 | 0.47 |
| desGly(NH$_2$)$^9$d(CH$_2$)$_5$[D-Phe$^2$, Ile$^4$, Arg[NH(CH$_2$)$_4$NH$_2$]$^8$]VP | 0.10 | 0.47 | 0.29 |
| desGly(NH$_2$)$^9$d(CH$_2$)$_5$[D-Tyr(Et)$^2$, Ile$^4$, Arg[NH(CH$_2$)$_4$NH$_2$]$^8$]VP | 0.03 | 0.21 | 0.16 |
| desGly(NH$_2$)$^9$d(CH$_2$)$_5$[D-Phe$^2$, Ile$^4$, Arg(NHC$_4$H$_9$—n)$^8$]VP | 0.64 | 0.80 | |
| desGly(NH$_2$)$^9$d(CH$_2$)$_5$[D-Tyr(Et)$^2$, Ile$^4$, Arg(NHC$_4$H$_9$—n)$^8$]VP | 0.66 | 0.80 | 0.56 |
| desGly(NH$_2$)$^9$d(CH$_2$)$_5$[D-Tyr$^2$, Ile$^4$, Arg(NHCH$_2$CH$_2$NH$_2$)$^8$]VP | 0.00 | 0.56 | 0.18 |
| desGly(NH$_2$)$^9$d(CH$_2$)$_5$[D-Tyr(Et)$^2$, Ile$^4$, Arg(NHCH$_2$CH$_2$NH$_2$)$^8$]VP | 0.16 | 0.36 | 0.26 |
| desGly(NH$_2$)$^9$d(CH$_2$)$_5$[D-Phe$^2$, Ile$^4$]AVP | 0.45 | 0.64 | 0.41 |
| desGly(NH$_2$)$^9$d(CH$_2$)$_5$[D-Phe$^2$, Ile$^4$, Arg(NHCH$_2$CH$_2$NH$_2$)$^8$]VP | 0.17 | 0.33 | 0.30 |
| desGly(NH$_2$)$^9$d(CH$_2$)$_5$[Tyr(Me)$^2$, Arg(NHCH$_2$CH$_2$NH$_2$)$^8$]VP | 0.10 | 0.26 | 0.24 |
| desGly(NH$_2$)$^9$d(CH$_2$)$_5$[Tyr(Me)$^2$, Arg(NHMe)$^8$]VP | 0.28 | 0.51 | 0.32 |
| Compounds of Example 10(b) | | | |
| d(CH$_2$)$_5$[D-Tyr(Et)$^2$, Ile$^4$, Gly(NHCH$_2$CH$_2$NH$_2$)$^9$]AVP | 0.29 | 0.42 | 0.30 |
| d(CH$_2$)$_5$[D-Phe$^2$, Ile$^4$, Gly(NH$_2$CH$_2$CH$_2$NH$_2$)$^9$]AVP | 0.20 | 0.32 | 0.21 |
| d(CH$_2$)$_5$[D-Phe$^2$, Ile$^4$, Gly(NHMe)$^9$]AVP | 0.57 | 0.88 | 0.05 |
| d(CH$_2$)$_5$[D-(Tyr(Et)$^2$, Val$^4$, Gly(NHMe)$^9$]AVP | 0.15 | 0.20 | 0.24 |
| d(CH$_2$)$_5$[D-Tyr(Et)$^2$, Val$^4$, beta-Ala(NHMe)$^9$]AVP | 0.04 | 0.38 | 0.22 |
| d(CH$_2$)$_5$[D-Ile$^2$, Ile$^4$, Gly(NHEt)$^9$]AVP | 0.32 | 0.55 | 0.28 |
| d(CH$_2$)$_5$[D-Phe$^2$, Ile$^4$, Gly(NHCH$_2$CH$_2$OH)$^9$]AVP | 0.60 | 0.83 | 0.51 |
| d(CH$_2$)$_5$[D-Phe$^2$, Ile$^4$, Gly(NHCH$_2$CH$_2$NH$_2$)$^9$]AVP | 0.20 | 0.32 | 0.21 |
| d(CH$_2$)$_5$[D-Tyr(Et)$^2$,Ile$^4$, Gly(NHCH$_2$CH$_2$NH$_2$)$^9$]AVP | 0.29 | 0.42 | 0.30 |
| d(CH$_2$)$_5$[D-Phe$^2$, Ile$^4$, Gly(NHBu-n)$^9$]AVP | 0.70 | 0.88 | 0.72 |

TABLE 3-continued

| | $R_f$ | | |
|---|---|---|---|
| | BAW I | BAWP | BAW II |
| d(CH$_2$)$_5$[Tyr(Me)$^2$, Gly(NHBu-n)$^9$]AVP | 0.62 | 0.84 | 0.53 |
| d(CH$_2$)$_5$[Tyr(Me)$^2$, Gly(NHCH$_2$CH$_2$NH$_2$)$^9$]AVP | 0.06 | 0.27 | 0.26 |
| d(CH$_2$)$_5$[D-Tyr(Et)$^2$, Val$^4$, Ala(NHMe)$^9$]AVP | 0.00 | 0.48 | 0.27 |
| d(CH$_2$)$_5$[Tyr(Me)$^2$, Sar(NHMe)$^9$]AVP | 0.20 | 0.24 | 0.46 |
| Compound of Example 10(c) | | | |
| d(CH$_2$)$_5$[D-Phe$^2$, Ile$^4$, Gly$^9$]AVP-Gly(NH$_2$) | 0.11 | 0.52 | 0.30 |

TABLE 4

| | Anti-ADH Potency | | Anti-VP Potency | |
|---|---|---|---|---|
| | ED | pA$_2$ | ED | pA$_2$ |
| Compounds of Example 10(a) | | | | |
| desGly(NH$_2$)$^9$d(CH$_2$)[D-Phe$^2$, Ile$^4$, Arg(NHCH$_2$CH$_2$OH)$^8$]VP | 0.49 ± 0.12 | 8.17 ± 0.10 | 2.7 ± 0.8 | 7.45 ± 0.12 |
| desGly(NH$_2$)$^9$d(CH$_2$)$_5$[D-Tyr(Et)$^2$, Ile$^4$, Arg(NHCH$_2$CH$_2$OH)$^8$]VP | 1.04 ± 0.04 | 7.82 ± 0.06 | 0.93 ± 0.18 | 7.89 ± 0.09 |
| desGly(NH$_2$)$^9$d(CH$_2$)$_5$[D-Phe$^2$, Ile$^4$, Arg[NH(CH$_2$)$_4$NH$_2$]$^8$]VP | 0.53 ± 0.03 | 8.11 ± 0.03 | 1.8 ± 0.3 | 7.61 ± 0.08 |
| desGly(NH$_2$)$^9$d(CH$_2$)$_5$[D-Tyr(Et)$^2$, Ile$^4$, Arg[NH(CH$_2$)$_4$NH$_2$]$^8$]VP | 1.41 ± 0.15 | 7.68 ± 0.05 | 1.12 ± 0.09 | 7.78 ± 0.4 |
| desGly(NH$_2$)$^9$d(CH$_2$)$_5$[D-Phe$^2$, Ile$^4$, Arg(NHC$_4$H$_9$—n)$^8$]VP | +++ | | 5.2 ± 0.9 | 7.13 ± 0.08 |
| desGly(NH$_2$)$^9$d(CH$_2$)$_5$[D-Tyr(Et)$^2$, Ile$^4$, Arg(NHC$_4$H$_9$—n)$^8$]VP | 1.7 ± 0.3 | 7.62 ± 0.09 | 2.2 ± 0.4 | 7.51 ± 0.08 |
| desGly(NH$_2$)$^9$d(CH$_2$)$_5$[D-Tyr$^2$, Ile$^4$, Arg(NHCH$_2$CH$_2$NH$_2$)$^8$]VP | 1.12 ± 0.08 | 7.81 ± 0.06 | 0.73 ± 0.13 | 7.93 ± 0.08 |
| desGly(NH$_2$)$^9$d(CH$_2$)$_5$[D-Phe$^2$, Ile$^4$]AVP | 0.66 ± 0.17 | 8.05 ± 0.09 | 1.0 ± 0.1 | 7.84 ± 0.03 |
| desGly(NH$_2$)d(CH$_2$)$_5$[D-Tyr(Et)$^2$, Ile$^4$, Arg(NHCH$_2$CH$_2$NH$_2$)$^8$]VP | 0.77 ± 0.22 | 8.00 ± 0.12 | 0.32 ± 0.04 | 8.33 ± 0.06 |
| desGly(NH$_2$)$^9$d(CH$_2$)$_5$[D-Phe$^2$, Ile$^4$, Arg(NHCH$_2$CH$_2$NH$_2$)$^8$]VP | 0.55 ± 0.06 | 8.11 ± 0.06 | 0.88 ± 0.10 | 7.89 ± 0.04 |
| desGly(NH$_2$)$^9$d(CH$_2$)$_5$[Tyr(Me)$^2$, Arg(NHCH$_2$CH$_2$NH$_2$)$^8$]VP | ~3.3+ | ~6.3 | 0.12 ± 0.02 | 8.75 ± 0.06 |
| desGly(NH$_2$)$^9$d(CH$_2$)$_5$[Tyr(Me)$^2$, Arg(NHMe)$^8$]VP | ~0.002+ | ~5.9 | 0.12 ± 0.01 | 8.73 ± 0.02 |
| Compounds of Example 10(b) | | | | |
| d(CH$_2$)$_5$[D-Tyr(Et)$^2$, Ile$^4$, Gly(NHCH$_2$CH$_2$NH$_2$)$^9$]AVP | 0.93 ± 0.09 | 7.86 ± 0.04 | 0.58 ± 0.05 | 8.07 ± 0.03 |
| d(CH$_2$)$_5$[D-Phe$^2$, Ile$^4$, Gly(NH$_2$CH$_2$CH$_2$NH$_2$)$^9$]AVP | 0.57 ± 0.13 | 8.10 ± 0.10 | 1.8 ± 0.03 | 7.58 ± 0.07 |
| d(CH$_2$)$_5$[Tyr(Me)$^2$, Gly(NHCH$_2$CH$_2$NH$_2$)$^9$]AVP | ~16+ | ~6.6 | 0.27 ± 0.03 | 8.39 ± 0.05 |
| d(CH$_2$)$_5$[D-Phe$^2$, Ile$^4$, Gly(NHMe)$^9$]AVP | 0.59 ± 0.09 | 8.07 ± 0.07 | 12 ± 4 | 6.22 ± 0.10+ |
| d(CH$_2$)$_5$[D-(Tyr(Et)$^2$, Val$^4$, Gly(NHMe)$^9$]AVP | 2.0 ± 0.3 | 7.58 ± 0.06 | 1.3 ± 0.1 | 7.71 ± 0.04 |
| d(CH$_2$)$_5$[D-Tyr(Et)$^2$, Val$^4$, beta-Ala(NHMe)$^9$]AVP | 1.6 ± 0.1 | 7.61 ± 0.02 | 1.2 ± 0.1 | 7.77 ± 0.05 |
| d(CH$_2$)$_5$[D-Ile$^2$, Ile$^4$, Gly(NHEt)$^9$]AVP | 0.94 ± 0.11 | 7.86 ± 0.05 | 21 ± 6 | 6.54 ± 0.11 |
| d(CH$_2$)$_5$[D-Phe$^2$, Ile$^4$, Gly(NHCH$_2$CH$_2$OH)$^9$]AVP | 0.49 ± 0.15 | 8.20 ± 0.12 | 8.5 ± 1.5 | 6.92 ± 0.07 |
| d(CH$_2$)$_5$[D-Phe$^2$, Ile$^4$, Gly(NHCH$_2$CH$_2$NH$_2$)$^9$]AVP | 0.57 ± 0.13 | 8.10 ± 0.10 | 1.8 ± 0.3 | 7.58 ± 0.07 |
| d(CH$_2$)$_5$[D-Tyr(Et)$^2$, Ile$^4$, Gly(NHCH$_2$CH$_2$NH$_2$)$^9$]AVP | 0.93 ± 0.09 | 7.86 ± 0.04 | 0.58 ± 0.05 | 8.07 ± 0.03 |
| d(CH$_2$)$_5$[D-Phe$^2$, Ile$^4$, Gly(NHBu-n)$^9$]AVP | 1.5 ± 0.2 | 7.66 ± 0.05 | 11 ± 2 | 6.80 ± 0.08 |
| d(CH$_2$)$_5$[Tyr(Me)$^2$, Gly(NHBu-n)$^9$]AVP | ++ | | 0.38 ± 0.10 | 8.44 ± 0.07 |
| d(CH$_2$)$_5$[Tyr(Me)$^2$, Gly(NHCH$_2$CH$_2$NH$_2$)$^9$]AVP | 16 ± 2 | 6.64 ± 0.07 | 0.27 ± 0.03 | 8.39 ± 0.05 |
| d(CH$_2$)[D-Tyr(Et)$^2$, Val$^4$, Ala(NHMe)$^9$]AVP | 0.82 ± 0.11 | 7.92 ± 0.06 | 0.46 ± 0.05 | 8.17 ± 0.04 |
| d(CH$_2$)$_5$[Tyr(Me)$^2$, Sar(NHMe)$^9$]AVP | ~200+ | ~5.5 | 0.32 ± 0.02 | 8.31 ± 0.03 |
| Compound of Example 10(c) | | | | |
| d(CH$_2$)$_5$[D-Phe$^2$, Ile$^4$, Gly$^9$]AVP-Gly(NH$_2$) | 0.98 ± 0.09 | 7.83 ± 0.04 | 1.4 ± 0.3 | 7.72 ± 0.09 |

+ mixed
++ weak agonist (0.03 u/mg)
+++ weak agonist

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound of the formula

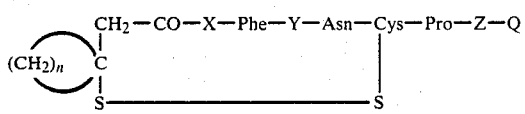

wherein n is 4 or 5; X is (D- or L-)Tyr(R), D-Phe, D-Val, D-Leu, D-Ile, D-Nva, D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Gln, Phe, Tyr, Gly, Abu or Leu; Z is (D- or L-) Arg, Orn or Lys; Q is NH(CH$_2$)$_p$NH$_2$, NH(CH$_2$)$_q$OH, NHalk or NHbzl; R is H, methyl ethyl, propyl or butyl, p is an integer from 3 to 6; q is an integer from 2 to 6; and alk is methyl, ethyl, propyl or butyl, provided that when Y is Val, Q is other than NHalk or NHbzl.

2. A compound of claim 1, wherein X is D-Phe.
3. A compound of claim 1, wherein X is D-Tyr(Et).
4. A compound of claim 1, wherein n is 5.
5. A compound of claim 1, wherein Y is Ile.
6. A compound of claim 1, wherein Y is Gln.
7. A compound of claim 1, wherein Y is Val.
8. A compound of claim 1, wherein Z is Arg.
9. A compound of claim 1, wherein Q is NHCH$_2$CH$_2$OH.
10. A compound of claim 1, wherein Q is NH(CH$_2$)$_4$NH$_2$.
11. A compound of claim 1, wherein Q is NHBu-n.
12. A compound of claim 1, wherein Q is NHMe.
13. [1-(beta-Mercapto-beta,beta-cyclopentamethylenepropionic acid), 2-D-phenylalanine, 4-isoleucine, 8-arginine-N-(beta-hydroxy)ethylamide, 9-desglycinamide] vasopressin, a compound of claim 1.
14. [1-(beta-Mercapto-beta,beta-cyclopentamethylenepropionic acid), 2-D-(O-ethyl)tyrosine, 4-isoleucine, 8-arginine-N-(beta-hydroxy)ethylamide, 9-desglycinamide] vasopressin, a compound of claim 1.

15. [1-(beta-Mercapto-beta,beta-cyclopentamethylenepropionic acid), 2-D-(O-ethyl)tyrosine, 4-isoleucine, 8-arginine-N-(delta-amino)butylamide, 9-desglycinamide] vasopressin, a compound of claim 1.

16. [1-(beta-Mercapto-beta,beta-cyclopentamethylenepropionic acid), 2-D-phenylalanine, 4-isoleucine, 8-arginine-N-(delta-amino)butylamide, 9-desglycinamide] vasopressin, a compound of claim 1.

17. [1-(beta-Mercapto-beta,beta-cyclopentamethylenepropionic acid), 2-D-phenylalanine, 4-isoleucine, 8-arginine-N-(n-butyl)amide, 9-desglycinamide] vasopressin, a compound of claim 1.

18. [1-(beta-Mercapto-beta,beta-cyclopentamethylenepropionic acid), 2-D-(O-ethyl)tyrosine, 4-isoleucine, 8-arginine-N-(n-butyl)amide, 9-desglycinamide] vasopressin, a compound of claim 1.

19. [1-(beta-Mercapto-beta,beta-cyclopentamethylenepropionic acid), 2-(O-methyl)tyrosine, 8-arginine-N-methylamide, 9-desglycinamide] vasopressin, a compound of claim 1.

20. A method for antagonizing the in vivo response of an animal to the antidiuretic and/or vasopressor action of an antidiuretic hormone, comprising administering to the animal being treated an amount of a compound of claim 1, in admixture with a physiologically and pharmaceutically acceptable carrier, effective to antagonize the antidiuretic and/or vasopressor responses to the antidiuretic hormone.

21. A compound of the formula

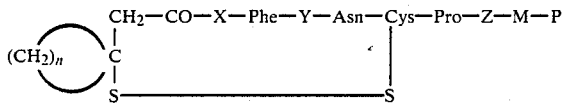

wherein n is 4 or 5; X is (D- or L-)Tyr(R), D-Phe, D-Val, D-Leu, D-Ile, D-Nva, D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Gln, Phe, Tyr, Gly, Abu or Leu; Z is (D- or L-)Arg, Orn or Lys; M is Gly, (D- or L-)beta-Ala, (D- or L-)Ala, Sar, Orn, Val, Phe, Ile, Thr, Pro, Tyr, Arg or Ser; P is NH(CH$_2$)$_{2-6}$NH$_2$, NH(CH$_2$)$_{2-6}$OH, NHalk, NHbzl or OH; R is H, methyl, ethyl, propyl or butyl; and alk is methyl, ethyl, propyl or butyl, provided that when M is Gly, P is other than OH and that when M is (D- or L-)-beta-Ala, P is also NH$_2$.

22. A compound of claim 21, wherein X is D-Phe.
23. A compound of claim 21, wherein X is D-Tyr(Et).
24. A compound of claim 21, wherein X is Tyr(Me).
25. A compound of claim 21, wherein X is D-Ile.
26. A compound of claim 21, wherein Y is Val.
27. A compound of claim 21, wherein Y is Ile.
28. A compound of claim 21, wherein Y is Gln.
29. A compound of claim 21, wherein Z is Arg.
30. A compound of claim 21, wherein M is Gly.
31. A compound of claim 21, wherein M is Ala.
32. A compound of claim 21, wherein M is Arg.
33. A compound of claim 21, wherein P is NHMe.
34. A compound of claim 21, wherein P is NHCH$_2$CH$_2$OH.
35. A compound of claim 21, wherein P is NHCH$_2$CH$_2$NH$_2$.

36. A compound of claim 21, wherein n is 5.
37. [1-(beta-Mercapto-beta,beta-cyclopentamethylenepropionic acid), 2-D-(O-ethyl)tyrosine, 4-valine, 9-glycine-N-(beta-amino)ethylamide]-arginine vasopressin, a compound of claim 21.

38. [1-(beta-Mercapto-beta,beta-cyclopentamethylenepropionic acid), 2-D-(O-ethyl)tyrosine, 4-valine, 9-alanine-N-methylamide]-arginine vasopressin, a compound of claim 21.

39. [1-(beta-Mercapto-beta,beta-cyclopentamethylenepropionic acid), 2-D-phenylalanine, 4-isoleucine, 9-glycine-N-(beta-amino)ethylamide]-arginine vasopressin, a compound of claim 21.

40. [1-(beta-Mercapto-beta,beta-cyclopentamethylenepropionic acid), 2-(O-methyl)tyrosine, 9-glycine-N-(beta-amino)ethylamide]-arginine vasopressin, a compound of claim 21.

41. [1-(beta-Mercapto-beta,beta-cyclopentamethylenepropionic acid), 2-D-phenylalanine, 4-isoleucine, 9-glycine-N-methylamide]-arginine vasopressin, a compound of claim 21.

42. [1-(beta-Mercapto-beta,beta-cyclopentamethylenepropionic acid), 2-D-(O-ethyl)tyrosine, 4-valine, 9-glycine-N-methylamide]-arginine vasopressin, a compound of claim 21.

43. [1-(beta-Mercapto-beta,beta-cyclopentamethylenepropionic acid), 2-D-isoleucine, 4-isoleucine, 9-glycine-N-ethylamide]-arginine vasopressin, a compound of claim 21.

44. [1-(beta-Mercapto-beta,beta-cyclopentamethylenepropionic acid), 2-D-phenylalanine, 4-isoleucine, 9-glycine-N-(beta-hydroxy)ethylamide]-arginine vasopressin, a compound of claim 21.

45. [1-(beta-Mercapto-beta,beta-cyclopentamethylenepropionic acid), 2-D-phenylalanine, 4-isoleucine, 9-glycine-N-(beta-amino)ethylamide]-arginine vasopressin, a compound of claim 21.

46. [1-(beta-Mercapto-beta,beta-cyclopentamethylenepropionic acid), 2-D-(O-ethyl)tyrosine, 4-isoleucine, 9-glycine-N-(beta-amino)ethylamide]-arginine vasopressin, a compound of claim 21.

47. [1-(beta-Mercapto-beta,beta-cyclopentamethylenepropionic acid), 2-D-phenylalanine, 4-isoleucine, 9-glycine-N-(n-butyl)amide]-arginine vasopressin, a compound of claim 21.

48. [1-(beta-Mercapto-beta,beta-cyclopentamethylenepropionic acid), 2-(O-methyl)tyrosine, 9-glycine-N-(n-butyl)amide]-arginine vasopressin, a compound of claim 21.

49. [1-(beta-Mercapto-beta,beta-cyclopentamethylenepropionic acid), 2-(O-methyl)tyrosine, 9-glycine-N-(beta-amino)ethylamide]-arginine vasopressin, a compound of claim 21.

50. [1-(beta-Mercapto-beta,beta-cyclopentamethylenepropionic acid), 2-D-(-ethyl)tyrosine, 4-valine, 9-beta-alanine-N-methylamide]-arginine vasopressin, a compound of claim 21.

51. A method for antagonizing the in vivo response of an animal to the antidiuretic and/or vasopressor action of an antidiuretic hormone, comprising administering to the animal being treated an amount of a compound of claim 21, in admixture with a physiologically and pharmaceutically acceptable carrier, effective to antagonize the antidiuretic and/or vasopressor responses to the antidiuretic hormone.

52. A compound of the formula

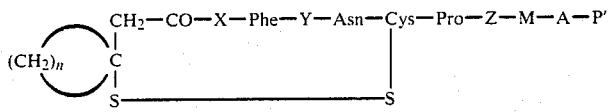

wherein n is 4 or 5; X is (D- or L-)Try(R), D-Phe, D-Val, D-Leu, D-Ile, D-Nva D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Gln, Phe, Tyr, Gly, Abu or Leu; Z is (D- or L-)Arg, Orn or Lys; M and A are independently selected from Gly, Orn, Val, Phe, Ile, Arg, Ser, Thr, Pro, (D- or L-)Ala, (D- or L-)-beta-Ala, Sar or Tyr; R is H, methyl, ethyl, propyl or butyl; and P' is OH, $NH_2$, NHalk, NHbzl, $NH(CH_2)_{2-6}NH_2$ or $NH(CH_2)_{2-6}OH$.

53. A compound of claim 52, wherein X is D-Phe.
54. A compound of claim 52, wherein n is 5.
55. A compound of claim 52, wherein Y is Ile.
56. A compound of claim 52, wherein Z is Arg.
57. A compound of claim 52, wherein M is Gly.
58. A compound of claim 52, wherein A is Gly.
59. A compound of claim 52, wherein A and M are each Gly.
60. A compound of claim 52, wherein P' is $NH_2$.
61. [1-(beta-Mercapto-beta,beta-cyclopentamethylenepropionic acid), 2-D-phenylalanine, 4-isoleucine, 9-glycine]-arginine vasopressyl glycinamide, a compound of claim 52.
62. A method for antagonizing the in vivo response of an animal to the antidiuretic and/or vasopressor action of an antidiuretic hormone, comprising administering to the animal being treated an amount of a compound of claim 52, in admixture with a physiologically and pharmaceutically acceptable carrier, effective to antagonize the antidiuretic and/or vasopressor responses to the antidiuretic hormone.

63. A compound of the formula

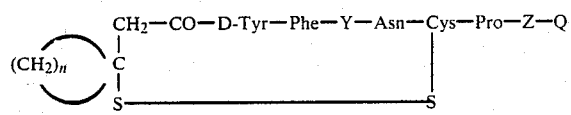

wherein n is 4 or 5; Y is Ile, Thr, Ala, Lys, Cha, Nva, Met, Nle, Orn, Ser, Asn, Phe, Tyr, Gly, Abu or Leu; Z is (D- or L-)Arg, Orn or Lys; and Q is $NH(CH_2)_{2-6}NH_2$ or $NH(CH_2)_{2-6}OH$.

64. A compound of claim 63, wherein n is 5.
65. A compound of claim 63, wherein Y is Ile.
66. A compound of claim 63, wherein Z is Arg.
67. A compound of claim 63, wherein Q is $NHCH_2CH_2NH_2$.
68. [1-(beta-Mercapto-beta,beta-cyclopentamethylenepropionic acid), 2-D-tyrosine, 4-isoleucine, 8-arginine-N-(beta-amino)ethylamide, 9-desglycinamide] vasopressin, a compound of claim 63.
69. A method for antagonizing the in vivo response of an animal to the antidiuretic and/or vasopressor action of an antidiuretic hormone, comprising administering to the animal being treated an amount of a compound of claim 63, in admixture with a physiologically and pharmaceutically acceptable carrier, effective to antagonize the antidiuretic and/or vasopressor responses to the antidiuretic hormone.

* * * * *